United States Patent
Gupta et al.

(10) Patent No.: US 6,927,193 B2
(45) Date of Patent: *Aug. 9, 2005

(54) ARYL ETHER DERIVATIVES AND PROCESSES FOR THEIR PREPARATION AND HERBICIDAL AND DESICCANT COMPOSITIONS CONTAINING THEM

(75) Inventors: Sandeep Gupta, Concord, OH (US); Masamitsu Tsukamoto, Mayfield Heights, OH (US); Mark Read, Willoughby, OH (US)

(73) Assignee: Ishihara Sangyo Kaisha, Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/376,621

(22) Filed: Mar. 3, 2003

(65) Prior Publication Data

US 2003/0195118 A1 Oct. 16, 2003

Related U.S. Application Data

(60) Division of application No. 10/001,816, filed on Dec. 5, 2001, now Pat. No. 6,613,718, which is a continuation-in-part of application No. 09/970,220, filed on Oct. 1, 2001, now abandoned.

(51) Int. Cl.$^7$ .................... C07D 239/56; C07D 239/58; C07D 239/47; A01N 43/54
(52) U.S. Cl. ....................... 504/243; 544/309; 544/318; 544/319; 544/320
(58) Field of Search ........................... 544/309; 504/243

(56) References Cited

U.S. PATENT DOCUMENTS

| | | | |
|---|---|---|---|
| 5,670,455 A | 9/1997 | Selby et al. | |
| 6,121,201 A | 9/2000 | Pulman et al. | |
| 6,355,799 B1 * | 3/2002 | Gupta et al. ................. | 544/309 |

FOREIGN PATENT DOCUMENTS

| | | |
|---|---|---|
| WO | WO 93/15074 | 8/1993 |
| WO | WO 96/07323 | 3/1996 |
| WO | WO 96/15115 | 3/1996 |
| WO | WO 96/98151 | 5/1996 |
| WO | WO 98/41093 | 9/1998 |
| WO | WO 99/14201 | 3/1999 |
| WO | WO 99/59983 | 11/1999 |
| WO | WO 00/12480 | 3/2000 |
| WO | WO00/32573 | 6/2000 |
| WO | WO 00/50409 | 8/2000 |

* cited by examiner

Primary Examiner—Venkataraman Balasubramanian
(74) Attorney, Agent, or Firm—Sughrue Mion, PLLC

(57) ABSTRACT

Substituted aryl ether derived compounds represented by the general structure (I) are described. X and Y are independent of each other and are represented by hydrogen, halogen, cyano, nitro, $(C_{1-4})$alkyl, $(C_{1-4})$haloalkyl, or $(C_{1-4})$haloalkoxy; Z is oxygen or sulfur; Q is selected form Q1 to Q6;

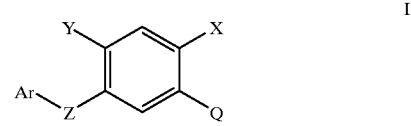

I

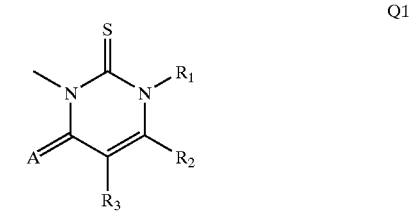

Q1

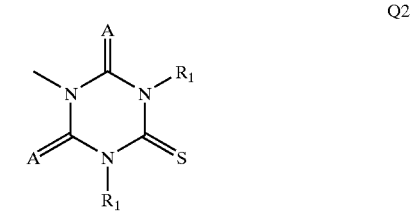

Q2

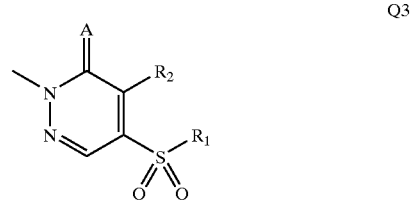

Q3

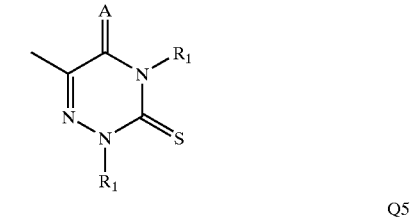

Q4

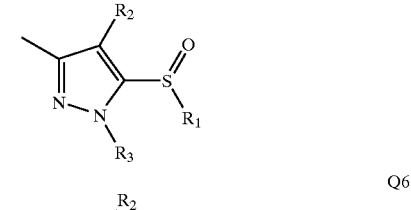

Q5

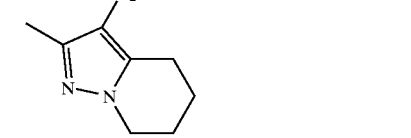

Q6

Also described are the processes for the manufacture of these compounds and agriculturally suitable compositions containing these as active ingredients which are useful as herbicides for general or selective pre-emergent or post-emergent control of undesired plant species and defoliants.

22 Claims, No Drawings

ARYL ETHER DERIVATIVES AND PROCESSES FOR THEIR PREPARATION AND HERBICIDAL AND DESICCANT COMPOSITIONS CONTAINING THEM

This is a divisional of application Ser. No. 10/001,816, filed Dec. 5, 2001, now U.S. Pat. No. 6,613,718, which is a Continuation-in-part of application Ser. No. 09/970,220, filed Oct. 1, 2001, which is abandoned; the disclosure of which is incorporated herein by reference.

TECHNICAL FIELD

The present invention relates to a class of aryl ether derivatives useful as herbicides and desiccants.

BACKGROUND OF THE INVENTION

Various substituted phenyl ethers (I') are known in literature. Q may be uracil, triazine, pyridazine, pyrazole, etc., R may be hydrogen, alkyl, cycloalkyl, alkenyl, or alkynyl. WO 98/41093 and U.S. Pat. No. 6,121,201 describe certain diaryl ethers as herbicides. WO 00/50409 describes herbicidal compounds containing 1-aryl-1,3,5-triazine-4-thione-2,6-dione derivatives. WO 99/14201 describes certain 2-phenyl-3(2H)-pyridazinone derivatives and WO 99/59983 describes certain 6-aryl-3,5-dithioxo-2,3,4,5-tetrahydro-1,2,4-triazine and 6-aryl-3-thioxo-5-oxo-2,3,4,5-tetrahydro-1,2,4-triazine derivatives as herbicides. WO 96/15115 and WO 00/12480 describes a group of substituted phenyl pyrazole derivatives as herbicides. WO 93/15074 and U.S. Pat. No. 5,670,455 describe certain aryl substituted fused pyrazole derivatives as herbicides.

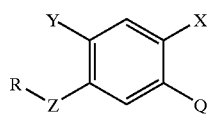

I'

WO96/07323 and WO96/08151 disclose some known uracil compounds. In WO96/07323 and WO96/08151, the generic representation is significantly broader than the disclosures set forth in them, and in the prior art patents.

However the specific aryl ether compounds of the formula (I) mentioned below are not known and are novel. Furthermore the present invention reveals that the aryl ether derivatives represented by the general formula (I) or their salts have potent herbicidal activity and/or desiccant activity with good crop safety.

SUMMARY OF THE INVENTION

This invention relates to aryl ether derivatives represented by the following general formula (I) and their salts:

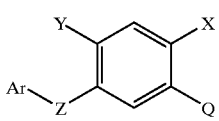

I wherein X and Y are independent of each other and are represented by hydrogen, halogen, cyano, nitro, $(C_{1-4})$alkyl, $(C_{1-4})$haloalkyl, or $(C_{1-4})$haloalkoxy;

Z is oxygen or sulfur;

Q is

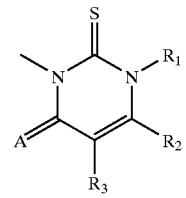

Q1

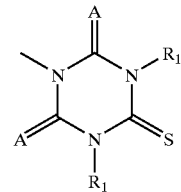

Q2

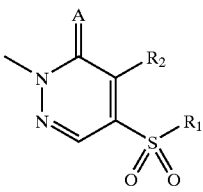

Q3

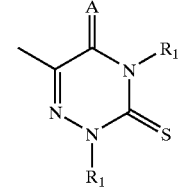

Q4

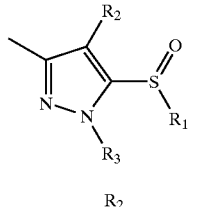

Q5

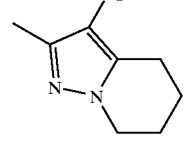

Q6

A is oxygen, sulfur, or imino;

$R_1$ is hydrogen, $(C_{1-4})$alkyl, or $(C_{1-4})$haloalkyl, and can be independent of each other;

$R_2$ and $R_3$ are independent of each other and may be selected from the group consisting of hydrogen, halogen, cyano, nitro, $(C_{1-4})$alkyl, $(C_{1-4})$haloalkyl, $(C_{2-6})$alkenyl, $(C_{2-6})$haloalkenyl and amino which may be optionally substituted with $(C_{1-4})$alkyl or $(C_{1-4})$haloalkyl;

Ar is substituted or unsubstituted carbocyclic or heterocyclic aromatic ring being at least a five or six membered ring. This ring can be fused with another substituted or unsubstituted five or six membered carbocyclic or heterocyclic ring; when Q is Q5, unsubstituted or substituted phenyl is excluded.

This invention also relates to herbicidal and/or desiccant compositions containing them, and to methods for using these compositions. Further this invention sometimes relates to methods for the control of undesired vegetation in a plantation crop by the application to the locus of the crop an effective amount of the compounds described herein, as broad spectrum herbicides which are effective against a variety of weed species in pre emergence and post emergence applications with crop safety. Furthermore this invention relates to methods for preparing these compounds and intermediates thereof

DETAILED DESCRIPTION OF THE INVENTION

The present invention provides the aryl ether compounds having the general formula (I) and salts thereof

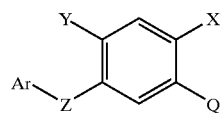

I wherein X, Y, Z, Ar, and Q are as described above.

The aryl in the definition of Ar may be a substituted or unsubstituted carbocyclic or heterocyclic aromatic ring being at least a five or six membered ring. This ring can be fused with another substituted or unsubstituted five or six membered carbocyclic or heterocyclic aromatic ring. For example, the carbocyclic aromatic ring in the definition of Ar may be aryl such as phenyl or naphthyl, and the heterocyclic aromatic ring in the definition of Ar may be a five or six membered ring having at least one heterogeneous atom of nitrogen, oxygen or sulfur, and for example may be pyridyl, pyrimidyl, pyridazinyl, triazolyl, thiazolyl, isothiazolyl, quinoline, or isoquinoline. The substituents for the substituted carbocyclic or heterocyclic aromatic ring in the definition of Ar may, for example, be halogen, $(C_{1-6})$ alkyl, halo$(C_{1-6})$alkyl, $(C_{1-6})$alkoxy, halo$(C_{1-6})$alkoxy, $(C_{1-6})$alkylthio, $(C_{1-6})$alkylsulfonyl, $(C_{1-6})$alkylsulfinyl, $(C_{1-6})$dialkylaminocarbonyl, cyano, nitro, amino, hydroxy, $(C_{1-6})$alkylsulfonylamino, $(C_{1-6})$alkoxycarbonyl$(C_{1-6})$alkoxy, $(C_{1-6})$alkoxycarbonyl-halo$(C_{1-6})$alkyl, $(C_{2-6})$alkenyloxycarbonyl$(C_{1-6})$alkoxy$(C_{1-6})$alkyl, $(C_{1-6})$alkylcarbonylamino, bisbenzoylamino, aminoacetyl, aminotrifluoroacetyl, or amino$(C_{1-6})$allylsulfonate. The number of substituents therefor is one or more, for example up to seven. When the number is two or more, the substituents may be same or different. When Q is Q5, unsubstituted or substituted phenyl is excluded.

Some compounds of formula (I) and their intermediates may occasionally exist as geometrical or optical isomers and the present invention includes all of these isomeric forms. Some compounds of the formula (I) and their intermediates may form a salt with an acidic substance or a basic substance. The salt with an acidic substance may be an inorganic acid salt such as a hydrochloride, a hydrobromide, a phosphate, a sulfate or a nitrate. The salt with a basic substance may be a salt of an inorganic or organic base such as a sodium salt, a potassium salt, a calcium salt, a quaternary ammonium salt such as ammonium salt or a dimethylamine salt.

The alkyl group and alkyl part in the definition related to X, Y, $R_1$ to $R_3$ and the substituents for the substituted aryl and heteroaryl ring as Ar have straight or branched chains with $C_{1-6}$, preferably $C_{1-4}$ such as methyl, ethyl, propyl, butyl, pentyl, or hexyl. The alkenyl group and their parts in the definition for $R_2$ and $R_3$ have also straight or branched chains with $C_{2-6}$, preferably $C_{2-4}$ such as vinyl, propenyl, butenyl, pentenyl or hexenyl.

The halogen atom and halogeno part in the definition related to X, Y, and $R_1$ to $R_3$ are fluorine, chlorine, bromine, or iodine. The haloalkyl or haloalkenyl group constitutes the alkyl or alkenyl group and one or more halogen atoms as mentioned above. When the number of halogen atom is two or more, halogen atoms may be same or different.

Preferred formula (I) compounds of this invention are those wherein

X, and Y are independently hydrogen, or halogen;
Z is oxygen or sulfur;
Q is selected from Q1, Q2, Q5, or Q6
Ar is pyridyl, pyrimidyl, triazolyl, thiazolyl, isothiazolyl, or phenyl; or each of pyridyl, pyrimidyl, triazolyl, thiazolyl, isothiazolyl, or phenyl being substituted with up to five substituents independently selected from bromine, chlorine, fluorine, iodine, $(C_1–C_4)$alkyl, halo$(C_{1-4})$alkyl, $(C_{1-4})$alkoxy, $(C_{1-4})$alkylthio, halo$(C_{1-4})$alkoxy, $(C_{1-4})$alkylsulfonyl, $(C_1-C_3)$alkylsulfinyl, di$(C_{1-4})$alkylaminocarbonyl, cyano, nitro, amino, hydroxy, $(C_{1-4})$alkylsulfonylamino, $(C_{1-4})$alkoxycarbonyl$(C_{1-4})$alkoxy, or $(C_{1-4})$alkoxycarbonylamino. When Q is Q5, unsubstituted or substituted phenyl is excluded.

The most preferred formula (I) compounds of this invention are those wherein

X is fluorine;
Y is chlorine;
Z is oxygen or sulfur;
Q is selected from Q1, Q2, or Q5.
Ar is 2-pyridyl, 3-pyridyl, 4-pyridyl, 3-bromo-2-pyridyl, 5-bromo-2-pyridyl, 6-bromo-2-pyridyl, 3-chloro-2-pyridyl, 5-chloro-2-pyridyl, 6-chloro-2-pyridyl, 3-fluoro-2-pyridyl, 5-fluoro-2-pyridyl, 6-fluoro-2-pyridyl, 3-cyano-2-pyridyl, 5-cyano-2-pyridyl, 6-2-pyridyl, 3-nitro-2-pyridyl, 5-nitro-2-pyridyl, 6-nitro-2-pyridyl, 3-trifluoromethyl-2-pyridyl, 4-trifluoromethyl-2-pyridyl, 5-trifluoromethyl-2-pyridyl, 6-trifluoromethyl-2-pyridyl, 5-amino-2-pyridyl, 3-dimethylaminocarbonyl-2-pyridyl, 3-methylsulfonyl-2-pyridyl, 3-isopropylsulfonyl-2-pyridyl, 6-chloro-3-trifluoromethyl-2-pyridyl, 3,5,6-trifluoropyridyl, 2-pyrimidyl, 4-pyrimidyl, 5-bromo-2-pyrimidyl, 4-chloro-2-pyrimidyl, 4-trifluoromethyl-2-pyrimidyl, 4,6-dimethoxy-2-pyrimidyl, 2,6-dimethoxy-4-pyrimidyl, 4,6-dimethoxy-2-triazinyl, phenyl, 2-iodophenyl, 2-trifluoromethoxyphenyl, 2-nitrophenyl, 4-nitrophenyl, 4-aminophenyl, 4-hydroxyphenyl, 4-methylsulfonylaminophenyl, 4-(1-ethoxycarbonylethoxy)phenyl, 2-cyanophenyl, 2-cyano-3-fluorophenyl, 2-cyano-4-fluorophenyl, 2-amino-4-(1-ethoxycarbonylethoxy)-phenyl, 2-cyano-4-nitrophenyl, 4-amino-2-cyanophenyl, 4-nitro-2-trifluoromethylphenyl, 4-amino-2-trifluoromethylphenyl, 4-acetylamino-2-trifluoromethylphenyl, 4-(1-ethoxycarbonylethoxy)-2-nitrophenyl, 5-chloro-4-(1-ethoxycarbonylethoxy)-2-nitrophenyl, 3-methyl-4-nitro-5-isothiazolyl,or 5-nitro-2-thiazolyl. When Q is Q5, unsubstituted or substituted phenyl is excluded.

The intermediate (III) can be prepared by the methods mentioned in Process 1. Starting materials (XIV) can be prepared according to the procedures described in the publications e.g. WO 98/41093 and WO 00/32573. The step requires treatment of the amine (XIV) with thiophosgene in a solvent such as hexane, heptane, benzene, toluene, xylene, or ethyl acetate in the presence of a base such as triethylamine, pyridine, lutidine, etc. The reaction temperature is usually from 0° C. to the reflux temperature of the mixture, preferably at the reflux temperature of the mixture. The reaction time is usually from 30 minutes to 6 hours, preferably from 2 to 3 hours. Alternatively, the aniline (XIV) can be converted into a salt of a dithiocarbamate by treatment with carbondisulfide in the presence of a base such as triethyl amine, pyridine, ethanolic aqueous ammonia, or sodium hydroxide. The dithiocarbamate can be converted into the isothiocyanate (III) by treatment with reagents such as ferrous sulfate, zinc sulfate, copper sulfate, or lead nitrate. The dithiocarbamate can also be converted into the isothiocyanate (III) by decomposition of a carboethoxy or a carbomethoxy derivative which can be prepared by treatment with ethylchloroformate or methylchloroformate.

Process 1

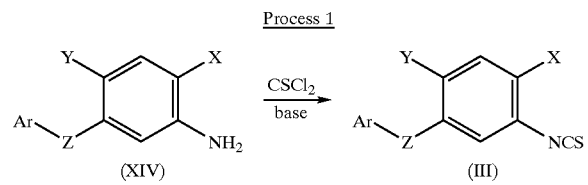

Process 2 is carried out by the reaction of a phenol (II) with an aryl halide or an heteroaryl halide with or without solvents. The solvents may include acetonitrile, tetrahydrofuran, dimethylsulfoxide, hexamethylphosphoric triamide, N,N-dimethylformamide, acetone, butan-2-one, benzene, toluene or xylene, in the presence of a base such as potassium carbonate, sodium carbonate, potassium hydroxide, sodium hydroxide, potassium t-butoxide, potassium fluoride, or sodium hydride. Catalysts may or may not be used. Such catalysts include copper(1)chloride, copper (1)oxide, copper, copper(1)alkoxide, alkyl cuprate, palladium(0), tetrabutylammonium halides, or 8-quinolinol. The reaction temperature is usually from 0° C. to 250° C., preferably from 20° C. to 120° C. The reaction time is usually from 1 to 12 hours, preferably from 2 to 6 hours. The aryl ether derivatives (I) may also be prepared by treatment of phenol (II) with aryl-lead tricarboxylates, triphenylbismuth-diacetate, triphenylbismuth-trifluoroacetate or diphenyliodonium halides in the presence of solvents such as benzene, toluene, dichloromethane, dichloroethane, chloroform or water, with or without catalysts such as copper, or a transition metal. The temperature is usually from 0° C. to the reflux temperature of the mixture, and the reaction time from 10 minutes to 72 hours. The temperature is preferably from 20° C. to the reflux temperature of the mixture, and the time preferably 2 to 6 hours.

The said phenol of formula (II) or its salt may be prepared by a similar process as disclosed in WO 98/41093 etc. or by a reaction of a compound having an alkyl or heteroaryl group except for the Ar group of the compound of the formula (I) with a hydrolytic agent such as borontribromide, lithium chloride, or hydrobromic acid, according to the conventional process.

Alternatively Process 2 may be carried out by the reaction of a halobenzene (XII) with an aryl or heteroaryl hydroxy compound or thiohydroxy compound in the similar reaction conditions.

Process 2

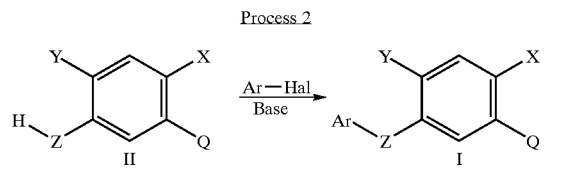

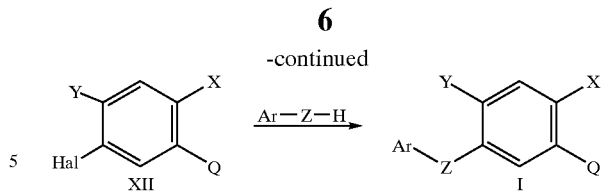

Using Process 3, an isothiocyanate (III) may be used to form the thionouracil (XV) by reacting the isothiocyanate (III) with an alkyl 3-methylamino-4,4,4-trifluorocrotonate and a base such as sodium hydride, sodium methoxide or sodium ethoxide, in a solvent such as dimethylsulfoxide, N,N-dimethylformamide, benzene, toluene, xylene, tetrahydrofuran, dioxane, or diethyl ether, at temperatures usually from −50° C. to 50° C., with a reaction time from 10 minutes to 14 hours, preferably between −30° C. to 30° C., with a reaction time of 15 minutes to 6 hours.

Alternatively Process 3 may be carried out by using a compound of the formula (V) having a radical; —NHC(S)—OR$_5$ (R$_5$; C$_{1-4}$alkyl or phenyl) except for the isothiocyanate group of the isothiocyanate of the formula (III) in the similar reaction conditions.

Process 3

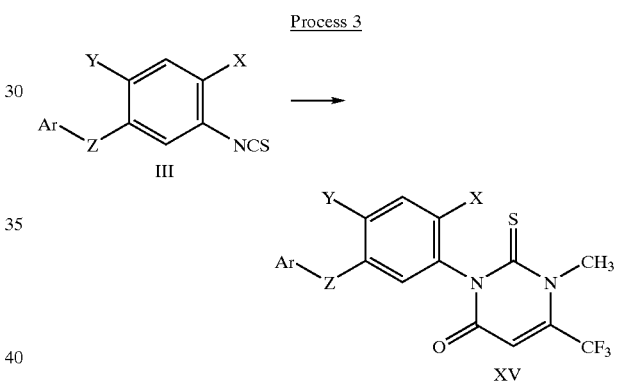

Using Process 4, a compound of formula (IX) can be prepared by reacting a compound of the formula (VIII), such as the above compound of formula (XV), with a thionating agent such as Lawesson's reagent or phosphorus pentasulfide. Further sulfurization may occur with prolonged heating and with excess reagent. The reaction uses solvents such as benzene, toluene and xylene. The reaction time is usually from 2 to 12 hours, preferably from 3 to 4 hours. The reaction temperature is usually from 0° C. to 150° C., preferably between 60° C. and the reflux temperature of the mixture.

Process 4

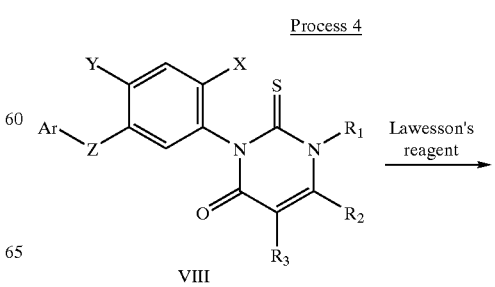

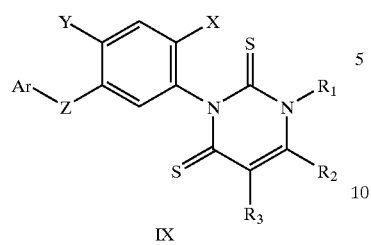

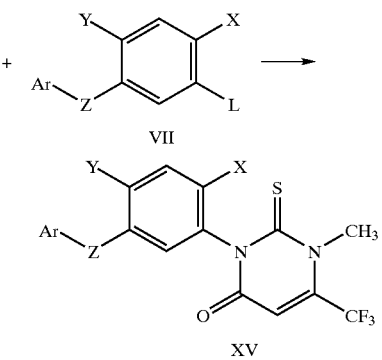

Process 5 is carried out in two stages. The first step is the formation of the (un)substituted benzyl uracil (XIX) via a compound (XVIII) from the corresponding benzyl amine (XVII) using the methodology described in Processes 1 and 3. The benzyl substituent at the 3 position of the uracil ring is removed by treatment with Lewis acids such as aluminium trichloride, zinc chloride, or ceric ammoniun nitrate in organic solvents such as toluene, xylene, chloro benzene, or acetonitrile to provide the uracil(VI). The reaction temperature is usually from 0° C. to 200° C., preferably from 20° C. to the reflux temperature of the mixture. The reaction time is from 1 to 24 hours, preferably from 2 to 12 hours.

Process 7 shows that the triazine ring in compound (XX) can be formed by reacting the isocyanate (X) with a thiourea derivative such as 1,3-dimethylthiourea and a carbonylation reagent such as phosgene, diphenylcarbonate, or N,N'-carbonyldi-imidazole. The reaction is carried out in the presence of a base such as triethyl amine, pyridine, or lutidine in a solvent such as N,N-dimethylformamide, toluene, xylene, tetrahydrofuran, dioxane, or methyl ethyl ketone, at temperatures usually from −20° C. to 120° C., with a reaction time from 1 hour to 24 hours, preferably from 20° C. to 80° C. with a reaction time of 2 hours to 6 hours.

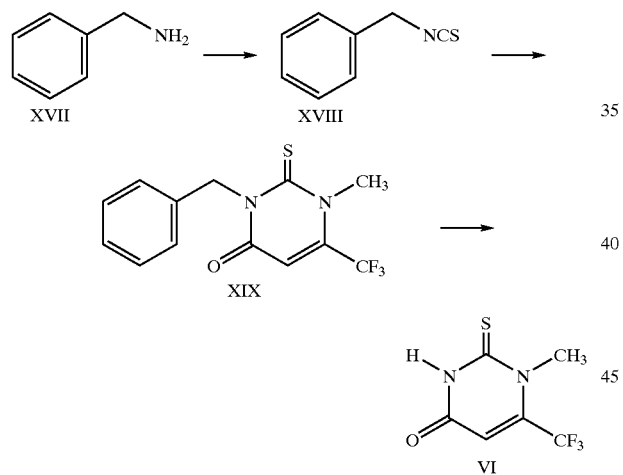

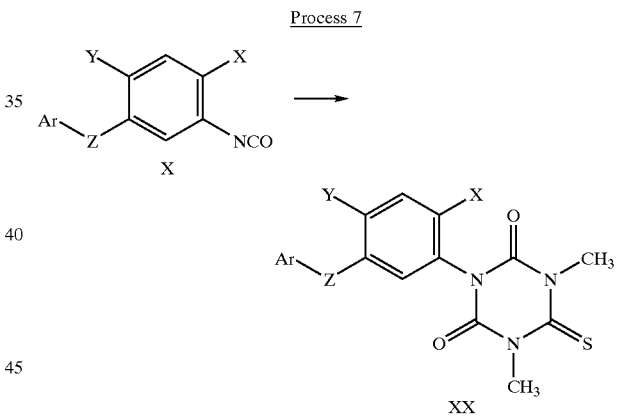

Process 6 shows that the uracil derivatives (XV) may be formed by reacting the prepared uracil (VI) with an aryl ether derivative (VII) carrying a leaving group represented by L. L can be substituents such as an activated halogen, a triflate, a tosyl group, or a nitro group. The reaction is carried out in the presence of an inorganic base such as sodium hydride, potassium carbonate, or an organic base such as triethyl amine, lutidine, or diazabicycloundecene in a solvent such as dimethylsulfoxide, N,N-dimethylformamide, benzene, toluene, xylene, tetrahydrofuran, dioxane, methyl ethyl ketone or diethyl ether, at temperatures usually from −20° C. to 160° C., with a reaction time from 1 hour to 12 hours, preferably from 0° C. to 130° C., with a reaction time of 1 hour to 6 hours.

Process 8 is carried out in four stages. The first step is the formation of the pyridazone ring system through a condensation of the corresponding phenylhydrazine, (XXI), with mucochloric acid with or without solvents. Examples of solvents for this reaction include methanol, ethanol, toluene, tetrahydrofuran, dioxane, etc. Reaction temperatures range between 40° C. to 200° C., preferably from 60° C. to 100° C., and reaction times range between 2 to 48 hours, preferably from 12 to 16 hours.

In the second step, the pyridazone compound, (XXII), is reacted with an inorganic salt of an alkyl mercaptan in an inert solvent such as tetrahydrofuran, 1,4-dioxane, benzene, toluene, N,N-dimethylformamide, or dimethyl sulfoxide to form the compound (XXIII). The reaction temperature is usually from 0° C. to 100° C., preferably ambient temperature, and a reaction time usually from 10 minutes to 6 hours, preferably 30 minutes to 1 hour.

The sulfone (XXIV) is obtained by oxidation of compound (XXIII) with such oxidizing agents as peroxides or oxone usually in a halogenated solvent such as methylene chloride, chloroform, or carbon tetrachloride. The reaction time is usually from 10 minutes to 6 hours, preferably from 1 to 2 hours, and the reaction temperature is usually from 0° C. to 100° C., preferably ambient temperature.

The final step is the halogen exchange reaction with nucleophiles leading to the pyridazone compound (XXV). Examples of the nucleophiles include methanolic ammonia, sodamide, ammonia, etc. The solvent is usually an inert solvent such as tetrahydrofuran, 1,4-dioxane, benzene, toluene, xylene, or N,N-dimethylformamide. The reaction temperature is usually between 0° C. and 200° C., preferably between 40° C. to 60° C., with a reaction time between 2 to 48 hours, preferably from 2 to 12 hours.

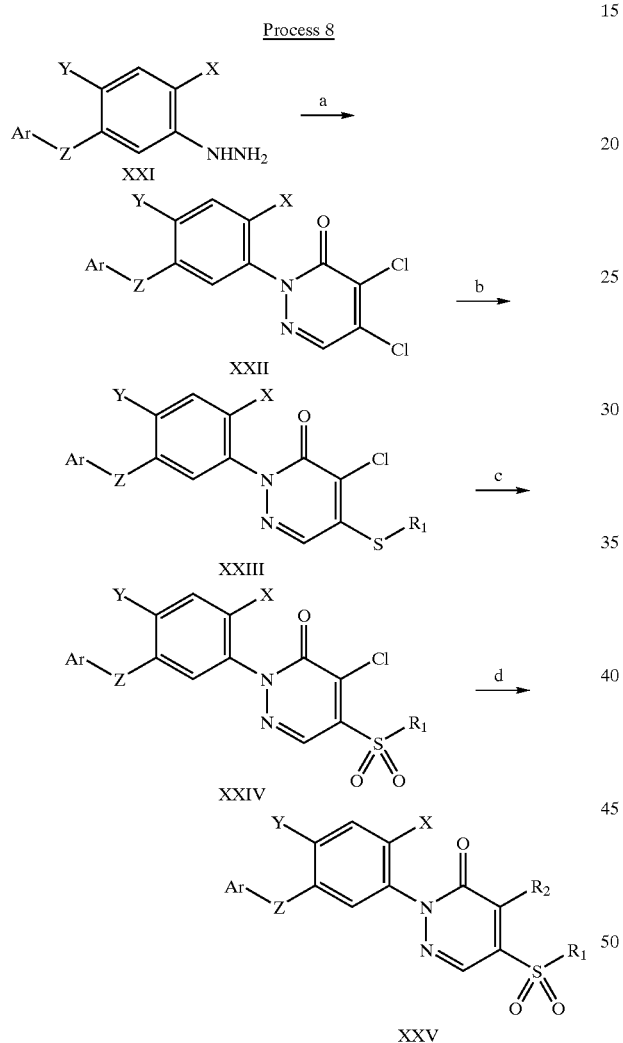

ether (XIV, A=H) with reagents such as chlorine, bromine, N-chlorosuccinimide, N-bromosuccinimide, and N-iodosuccinimide. The reaction can be carried out in organic solvents such as N,N-dimethylformamide, dimethylsulfoxide, chloroform, or dichloromethane at temperatures of from −20° C. to 150° C., preferably from 10° C. to 80° C. The reaction time is from 1 to 24 hours, preferably from 2 to 12 hours.

The second step is the formation of the Grignard reagent followed by treatment with an acid halide derived from a monoalkyl ester of oxalic acid. The Grignard reagent is formed with magnesium in an aprotic solvent such as diethyl ether, tetrahydrofuran, dioxane, benzene, toluene, xylene, etc. at temperatures from 0° C. to 100° C., preferably from 10° C. to 60° C., with or without catalytic amounts of iodine. Reaction times are usually from 10 minutes to 24 hours, preferably from 0.5 to 2 hours. The Grignard reagent is treated with an acid halide derived from a monoalkyl ester of oxalic acid such as ethyl chlorooxoacetate to form (un) substituted thiosemicarbizides (XXVIII). The reaction time during and after the addition is from 1 to 24 hours, preferably from 2 to 12 hours at temperatures of from −110° C. to 100° C., preferably from −80° C. to 25° C.

The third step is the formation of the 1,2,4-triazine (XXVIII) by condensation of (un)substituted thiosemicarbizides (XXVII). The solvent may include protic solvents, such as methanol, ethanol, isopropanol, etc. for a reaction time usually from 2 to 48 hours, preferably from 2 to 12 hours and a reaction temperature of from 0° C. to 200° C., preferably between 40° C. and the reflux temperature of the solvent.

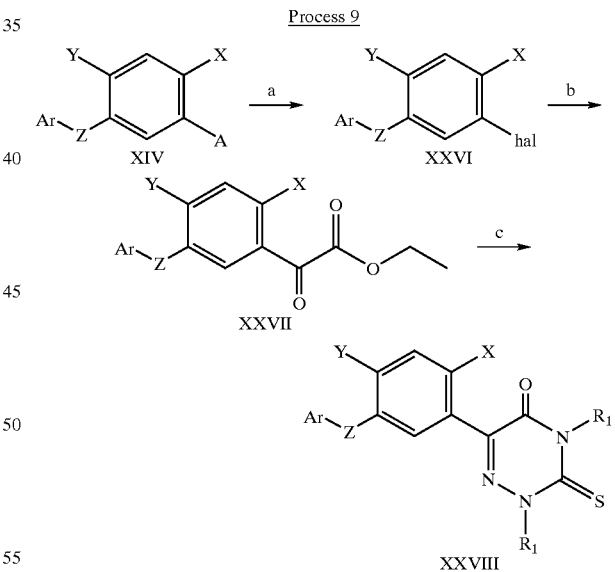

Process 9 is carried out in three stages. The first step is the formation of compound (XXVI) from the corresponding substituted aniline (XIV, A=NH₂) by diazotization of the amine followed by conversion to the halide by treatment with an inorganic halide such as sodium iodide, potassium iodide, sodium bromide, or potassium bromide. The reaction can be carried out in aqueous acids such as hydrochloric acid, sulfuric acid, or acetic acid at temperatures of from −40° C. to 80° C., preferably from 0° C. to 10° C., and the reaction time is from 10 minutes to 12 hours, preferably from 0.5 to 2 hours. Alternatively, compound (XXVI) can be prepared by direct halogenation of the corresponding aryl Process 10 shows that compounds (XXX) can be prepared by oxidizing starting materials such as compounds (XXIX). The reaction is carried out in the presence of an oxidizing agent such as hydrogen peroxide or m-chloroperbenzoic acid in a solvent such as chloroform, toluene, or ether such as diethyl ether, at temperature from −20° C. to 250° C., with a reaction time from 0.5 to 36 hours, preferably from 20° C. to 150° C. with a reaction time of 1 to 24 hours. The said compounds (XXIX) or their salts may be prepared by a similar process as disclosed in WO 98/41093 etc.

Process 10

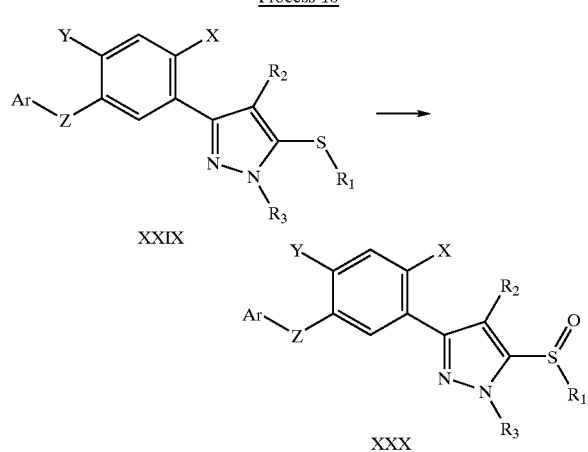

The synthesis of compounds (XXXIV) proceeds in 3 stages (a–c) as shown in Process 11. Compounds (XXXI) can be prepared by reaction between compounds (XXVI) and acetylene derivatives such as trimethylsilyl acetylene, in the presence of a metal catalyst such as bis(triphenylphosphine)palladium chloride with a co-catalyst such as copper iodide in a solvent such as toluene, xylene or triethylamine, at temperatures from −20° C. to 200° C., with a reaction time from 0.5 to 24 hours, preferably from 20° C. 150° C. with a reaction time from 1 to 12 hours. The second step is the formation of compounds (XXXIII) from the corresponding compounds (XXXI). The reaction is carried out in the presence of compounds (XXXII) in an inert solvent such as toluene, xylene or biphenyl, at a temperature from 0° C. to 300° C., preferably from 50° C. to 200° C. The reaction time is usually from 1 to 72 hours, preferably 2 to 12 hours. The third step is the synthesis of compounds (XXXIV) from the corresponding compounds (XXXIII). The reaction is carried out in the presence of halogenating reagent such as chlorine, N-chlorosuccinimde, bromine or N-bromosuccinimide in a solvent such as N,N-dimethylformamide, at temperature from 0° C. to 200° C., preferably 20° C. to 150° C. The reaction time is 0.5 to 24 hours, preferably 1 to 6 hours.

Process 11

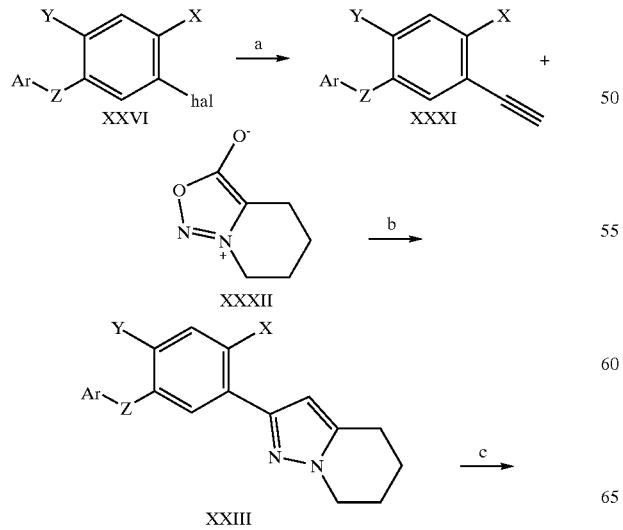

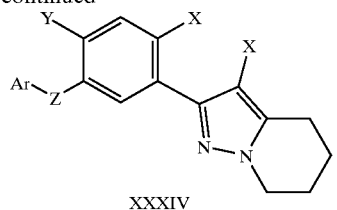

Process 12 shows that a compound of the formula (I), with Q as Q1, can be prepared by reacting a compound of the formula (VIII') ($R_1$ is hydrogen) with an alkylating reagent such as an alkyl halide or haloalkyl halide in the presence or absence of a base, according to the conventional reaction conditions.

Process 12

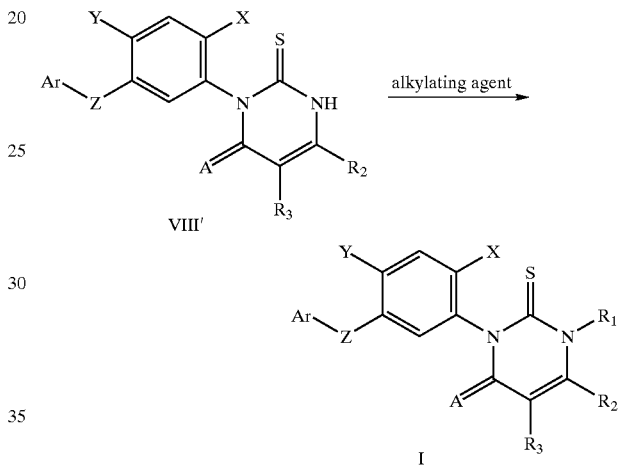

Although some embodiments of the present invention are described as follows, the scope of the present invention is not limited to such an embodiment. Preparation examples for the compounds of the present invention will be described.

EXAMPLE 1

3-[4-Chloro-2-fluoro-5-(2-pyrimidinyloxy)phenyl]-2,3-dihydro-1-methyl-2-thioxo -6-(trifluoromethyl)-4(1H)-pyrimidinone (Compound no. 1-1)

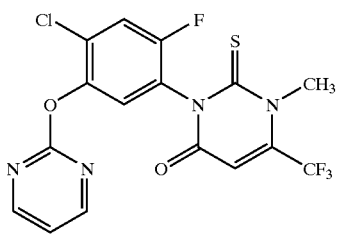

(1) 4-Chloro-2-fluoro-5-(2-pyrimidinyloxy)-benzenamine (50 g) and triethyl amine (42.2 g) were dissolved in anhydrous ethyl acetate (400 ml) and stirred under ice cooling. Thiophosgene (74.3 g) dissolved in ethyl acetate (400 ml) was slowly added to the stirred solution. The mixture was heated at reflux for 2 hr and filtered. Evaporation of the solvent afforded 2-(2-chloro-4-fluoro-5- isothiocyanatophenoxy)-pyrimidine which was used for the next step without purification. ¹H NMR, CDCl₃, 7.12 (1H, t, J=4.7 Hz), 7.13 (1H, d, J=7.0 Hz), 7.32 (1H, d, J=8.9 Hz), 8.58 (2H, t, J=4.7 Hz).

Ethyl 4,4,4-trifluoro-3-(methylamino)but-2-ennoate (42.4 g) in toluene (150 ml) was slowly added to a stirred suspension of sodium hydride (60%, 8.4 g) in anhydrous N,N-dimethylformamide (150 ml) at −10° C. The solution was stirred for 0.5 hr at this temperature and cooled to −50° C. The above isothiocyanate dissolved in toluene (150 ml) was added drop wise to the stirred solution while maintaining the temperature at −50° C. The solution was allowed to warm to −20° C. and stirred for 2 hr. After neutralization with dilute hydrochloric acid, the solution was partitioned between water and ethyl acetate, separated, dried (Na₂SO₄) and the organic layer evaporated to give the crude product. Column chromatography over silica gel (eluent, methylene chloride:ethyl acetate, 96:4) followed by crystallization from ether-hexane afforded the title compound (44.3 g).

(2) 4-Chloro-2-fluoro-5-(2-pyrimidinyloxy)benzenamine (1.0 g) was dissolved in anhydrous ethyl acetate (50 ml) and thiophosgene (0.59 g) was slowly added to the stirred solution. The mixture was heated at reflux for 2 hr. Evaporation of the solvent afforded 2-(2-chloro-4-fluoro-5-isothiocyanatophenoxy)pyrimidine.

Ethyl 4,4,4-trifluoro-3-(methylamino)but-2-enoate (0.94 g) in anhydrous N,N-dimethylformamide (25 ml) was slowly added to a stirred suspension of sodium hydride (60%, 0.18 g) in anhydrous N,N-dimethylformamide (25 ml) at −20° C. The solution was stirred for 0.5 hr at this temperature and cooled to −50° C. The above isothiocyanate dissolved in anhydrous N,N-dimethylformamide (25 ml) was added drop wise to the stirred solution while maintaining the temperature at −50° C. The solution was allowed to warm to −20° C. and stirred for 2 hr. After neutralization with dilute hydrochloric acid, the solution was partitioned between water and ethyl acetate, separated, dried (Na₂SO₄) and the organic layer evaporated. NMR of this residue indicated it to be a mixture containing uncyclized intermediates. The residue was dissolved in toluene (50 ml), triethylamine (1 g) was added and the solution was heated at reflux for 0.5 hr. Evaporation of the solvent afforded a residue which was subjected to column chromatography over silica gel (eluent, hexane:ethyl acetate, 7:3) to afford the title compound (1.36 g).

EXAMPLE 2

3-[4-Chloro-2-fluoro-5-(2-pyrimidinyloxy)phenyl]-5,6-dihydro-1,5-dimethyl-6-thioxo -1,3,5-triazine-2,4(1H,3H)-dione (Compound no. 2-1)

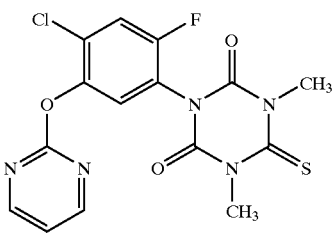

4-Chloro-2-fluoro-5-(2-pyrimidinyloxy) benzenamine (2 g) and triethyl amine (1.7 g) were dissolved in anhydrous ethyl acetate (75 ml) and stirred under ice cooling. Triphosgene (2.5 g) dissolved in ethyl acetate (75 ml) was slowly added to the stirred solution. The solution was heated at reflux for 2 hr and filtered. Evaporation of the solvent afforded 2-(2-chloro-4-fluoro-5-isocyanatophenoxy)-pyrimidine which was used for the next step without further purification.

The above isocyanate was dissolved in anhydrous toluene (21 ml) and triethyl amine (1 ml), 1,3-dimethyl-2-thiourea (0.87 g), 1,1'-carbonyldiimidazole (2.7 g) were added. The solution was stirred at 85° C. for 6 hr and the product was partitioned between water and ethyl acetate. The organic phase was separated, dried, evaporated and the residue chromatographed on silica gel (eluent, hexane:ethyl acetate, 6:4) to afford the title compound (2.7 g).

EXAMPLE 3

2,3-Dihydro-1-methyl-3-(phenylmethyl)-2-thioxo-6-(trifluoromethyl)-4(1H)-pyrimidinone

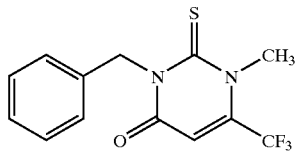

Benzylamine (1.5 g) and triethyl amine (2.9 g) were dissolved in anhydrous ethyl acetate (50 ml) and stirred under ice cooling. Thiophosgene (4.9 g) dissolved in ethyl acetate (50 ml) was slowly added to the stirred solution. The solution was heated at reflux for 2 hr and filtered. Evaporation of the solvent afforded (isothiocyanatomethyl)-benzene which was used in the next step without purification. ¹H NMR, CDCl₃, 4.72 (2H, s), 7.30–7.40 (5H, m).

4,4,4-Trifluoro-3-(methylamino)-2-butenoic acid, ethyl ester, (2Z)-(1.43 g) in toluene (25 ml) was slowly added to a stirred suspension of sodium hydride (60%, 0.28 g) in anhydrous N,N-dimethylformamide (25 ml) at −10° C. The solution was stirred for 0.5 hr at this temperature and cooled to −50° C. The above isothiocyanate dissolved in toluene (25 ml) was added drop wise with stirring to the solution, while maintaining the temperature at −50° C. The solution was then allowed to warm to −20° C. and stirred for 2 hr. After neutralization with dilute hydrochloric acid, the solution was partitioned between water and ethyl acetate and the organic layer was evaporated to furnish a crude product. Column chromatography over silica gel (eluent, hexane:ethyl acetate, 90:10) afforded the title compound (2.6 g). ¹H NMR, CDCl₃, 3.86 (3H, m), 5.74 (2H, s), 6.51 (1H, s), 7.27–7.30 (3H, m), 7.42–7.46 (2H, m).

EXAMPLE 4

2,3-Dihydro-1-methyl-2-thioxo-6-(trifluoromethyl)-4(1H)-pyrimidinone

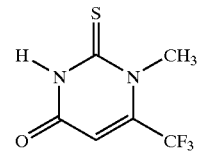

2,3-Dihydro-1-methyl-3-(phenylmethyl)-2-thioxo-6-(trifluoromethyl)-4(1H)-pyrimidinone (1.0 g) was dissolved in m-xylene (15 ml) and anhydrous aluminum chloride (0.58 g) was added. The solution was refluxed for 4 hr and poured onto ice water. Extraction with ethyl acetate and evaporation of the solvent in vacuo afforded a residue which was triturated with diethyl ether to afford the title compound (0.34 g). $^1$H NMR, CDCl$_3$, 3.86 (3H, m), 6.49 (1H, s), 10.62 (1H, br s).

EXAMPLE 5

6-[4-Chloro-2-fluoro-5-(2-pyrimidinyloxy)phenyl]-3,4-dihydro-2,4-dimethyl-3-thioxo -1,2,4-triazin-5 (2H)-one (Compound no. 4-1)

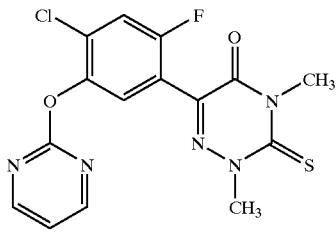

A solution of 2,4-dimethylthiosemicarbazide (0.20 g) and 2-(4-chloro-2-fluoro-5-methoxyphenyl)-2-oxoacetic acid (0.38 g) in methanol (10 ml) was refluxed for 16 hours. Filtration of the reaction mixture afforded 6-(4-chloro-2-fluoro-5-methoxy-phenyl)-2,4-dimethyl-5-oxo-3-thioxo-2,3,4,5-tetrahydro-1,2,4-triazine (0.28 g). $^1$H NMR, CDCl$_3$, 3.77 (3H, s), 3.91 (3H, s), 4.07 (3H, s), 7.08 (1H, d, J=6.09 Hz), 7.25 (1H, d, J=9.22 Hz).

Boron tribromide-methyl sulfide complex (5.26 g, 97%) was added in portions to a refluxing solution of the above compound (0.28 g) in 1,2-dichloroethane (20 ml). After refluxing for 20 hours, the reaction mixture was diluted with methylene chloride and washed with water. The organic layer was dried over magnesium sulfate and concentrated to give 6-(4-chloro-2-fluoro-5-hydroxyphenyl)-2,4-dimethyl-5-oxo-3-thioxo-2,3,4,5-tetrahydro-1,2,4-triazine (0.26 g). $^1$H NMR, CDCl$_3$, 3.77 (3H, s), 4.06 (3H, s), 5.49 (1H, bs), 7.18–7.20 (2H, m).

A mixture 6-(4-chloro-2-fluoro-5-hydroxyphenyl)-2,4-dimethyl-5-oxo-3-thioxo-2,3,4,5-tetrahydro-1,2,4-triazine (0.200 g), 2-chloropyrimidine (0.084 g), potassium carbonate (0.113 g), 2-butanone (10 ml), and dimethyl sulfoxide (2.5 ml) was heated at refluxed for 10 hours. The reaction was partitioned between water and ethyl acetate and the aqueous phase extracted with ethyl acetate (3×25 ml). The combined organic layers were dried over anhydrous magnesium sulfate and concentrated to afford the desired material (0.21 g).

EXAMPLE 6

2-[2-Chloro-5-[4-chloro-5-[(difluoromethyl) sulfinyl]-1-methyl-1H-pyrazol-3-4-fluorophenoxy]-pyrimidine (Compound no. 5-1)

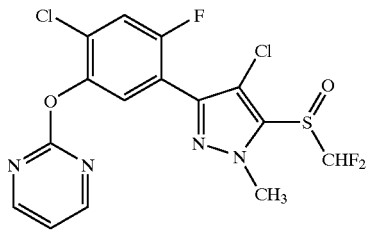

A mixture of 2-chloropyrimidine (150 mg), 2-chloro-5-[4-chloro-5-[(difluoromethyl)-thio]-1-methyl-1H-pyrazol-3-yl]-4-fluorophenol (0.3 g) and potassium carbonate (0.18 g) in N,N-dimethylformamide and methyl ethyl ketone (1:4, 20 ml) was heated at reflux overnight. The resulting mixture was allowed to cool to room temperature and partitioned between ethyl acetate and brine. The organic layer was washed with brine and dried over anhydrous sodium sulfate. The organic solution was concentrated in vacuo and the residue purified by column chromatography on silica gel (eluent, ethyl acetate:hexane, 2:3) to give 2-[2-chloro-5-[4-chloro-5-[(difluoromethyl)thio)-1-methyl-1H-pyrazol-3-yl]-4-fluorophenoxy]pyrimidine, (0.29 g).

A mixture of 2-[2-chloro-5-[4-chloro-5-[(difluoromethyl) thio]-1-methyl-1H-pyrazol-3-yl]-4-fluorophenoxy] pyrimidine (0.23 g) and m-chloroperbenzoic acid (70%, 0.14 g) in chloroform (15 ml) was heated at reflux for 12 hours. The mixture was allowed to cool to room temperature and concentrated in vacuo. The residue was chromatographed on silica gel (eluent, ethyl acetate:hexane, 1:2 to 2:3) to give the desired compound (45 mg) as a colorless oil.

EXAMPLE 7

3-Chloro-2-[4-chloro-2-fluoro-5-(2-pyrimidinyloxy) phenyl]-4,5,6,7-tetrahydro-pyrazolo[1,5-a]pyridine (Compound no. 6-1)

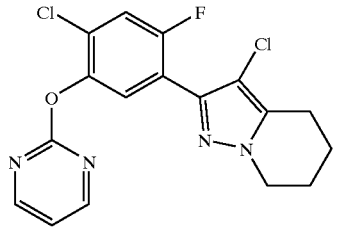

A mixture of 2-chloro-4-fluoro-5-(4,5,6,7-tetrahydropyrazolo[1,5-a]pyridin-2-yl)-phenol (5.0 g) and N-chlorosuccinimide (2.65 g) in N,N-dimethylformamide (30 ml) was stirred at 65° C. for 2 hours. The resulting mixture was poured into water and the precipitate was collected by filtration and dried. 2-Chloro-5-(3-chloro-4,5,6,7-tetrahydropyrazolo[1,5-a]pyridin-2-yl)-4-fluorophenol (5.50 g) was obtained as a white solid.

To a solution of 2-chloro-5-(3-chloro-4,5,6,7-tetrahydropyrazolo[1,5-a]pyridin-2-yl)-4-fluorophenol (0.5 g) and 2-chloropyrimidine (0.25 g), in a mixed solvent of 2-butanone:dimethylsulfoxide (1:4) (50 ml) was added potassium carbonate (0.35 g) at room temperature. After addition, the mixture was heated at reflux for 12 hours under a nitrogen atmosphere. The mixture was allowed to cool to room temperature and partitioned between ethyl acetate and brine. The organic phase was washed with brine (×2) and dried over anhydrous sodium sulfate. The solvent was removed in vacuo and the residue was purified by column chromatography on silica gel (eluent, ethyl acetate:hexane, 2:1) to give the desired compound (0.47 g).

Using the procedures as described in Schemes and Examples 1–7, the compounds of this invention can be readily prepared. Tables I–VI list structures for a few representative compounds of this invention.

TABLE I

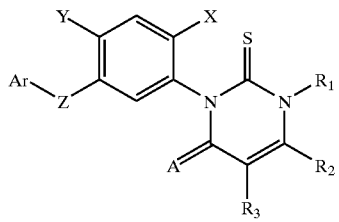

| No. | Ar | X | Y | Z | $R_1$ | $R_2$ | $R_3$ | A |
|---|---|---|---|---|---|---|---|---|
| 1-1 | 2-pyrimidyl | F | Cl | O | $CH_3$ | $CF_3$ | H | O |
| 1-2 | 4-chloro-2-pyrimidyl | F | Cl | O | $CH_3$ | $CF_3$ | H | O |
| 1-3 | 4,6-dimethoxy-2-pyrimidyl | F | Cl | O | $CH_3$ | $CF_3$ | H | O |
| 1-4 | 5-bromo-2-pyrimidyl | F | Cl | O | $CH_3$ | $CF_3$ | H | O |
| 1-5 | 6-chloro-5-nitro-4-pyrimidyl | F | Cl | O | $CH_3$ | $CF_3$ | H | O |
| 1-6 | 6-chloro-4-pyridazinyl | F | Cl | O | $CH_3$ | $CF_3$ | H | O |
| 1-7 | 6-chloro-3-pyridazinyl | F | Cl | O | $CH_3$ | $CF_3$ | H | O |
| 1-8 | 2-pyridyl | F | Cl | O | $CH_3$ | $CF_3$ | H | O |
| 1-9 | 3-nitro-2-pyridyl | F | Cl | O | $CH_3$ | $CF_3$ | H | O |
| 1-10 | 5-bromo-2-pyridyl | F | Cl | O | $CH_3$ | $CF_3$ | H | O |
| 1-11 | 5-chloro-2-pyridyl | F | Cl | O | $CH_3$ | $CF_3$ | H | O |
| 1-12 | 6-fluoro-2-pyridyl | F | Cl | O | $CH_3$ | $CF_3$ | H | O |
| 1-13 | 6-chloro-2-pyridyl | F | Cl | O | $CH_3$ | $CF_3$ | H | O |
| 1-14 | 3,5,6-trifluoro-2-pyridyl | F | Cl | O | $CH_3$ | $CF_3$ | H | O |
| 1-15 | 3-trifluoromethyl-2-pyridyl | F | Cl | O | $CH_3$ | $CF_3$ | H | O |
| 1-16 | 4-trifluoromethyl-2-pyridyl | F | Cl | O | $CH_3$ | $CF_3$ | H | O |
| 1-17 | 3-cyano-2-pyridyl | F | Cl | O | $CH_3$ | $CF_3$ | H | O |
| 1-18 | 5-cyano-2-pyridyl | F | Cl | O | $CH_3$ | $CF_3$ | H | O |
| 1-19 | 5-nitro-2-pyridyl | F | Cl | O | $CH_3$ | $CF_3$ | H | O |
| 1-20 | 3-ethylsulfonyl-2-pyridyl | F | Cl | O | $CH_3$ | $CF_3$ | H | O |
| 1-21 | 3-methylsulfonyl-2-pyridyl | F | Cl | O | $CH_3$ | $CF_3$ | H | O |
| 1-22 | 3-isopropylsulfonyl-2-pyridyl | F | Cl | O | $CH_3$ | $CF_3$ | H | O |
| 1-23 | 5-chloro-2-pyridyl | F | Cl | O | $CH_3$ | $CF_3$ | H | O |
| 1-24 | 3-nitro-2-pyridyl | F | Cl | O | $CH_3$ | $CF_3$ | H | O |
| 1-25 | 5-trifluoromethyl-2-pyridyl | F | Cl | O | $CH_3$ | $CF_3$ | H | O |
| 1-26 | 3-amino-2-pyridyl | F | Cl | O | $CH_3$ | $CF_3$ | H | O |
| 1-27 | 3-aminotrifluoroacetyl-2-pyridyl | F | Cl | O | $CH_3$ | $CF_3$ | H | O |
| 1-28 | 3-aminoacetyl-2-pyridyl | F | Cl | O | $CH_3$ | $CF_3$ | H | O |
| 1-29 | 3-aminomethylsulfonate-2-pyridyl | F | Cl | O | $CH_3$ | $CF_3$ | H | O |
| 1-30 | 3-chloro-2-pyridyl | F | Cl | O | $CH_3$ | $CF_3$ | H | O |
| 1-31 | 6-bromo-2-pyridyl | F | Cl | O | $CH_3$ | $CF_3$ | H | O |
| 1-32 | 5-chloro-3-trifluoromethyl-2-pyridyl | F | Cl | O | $CH_3$ | $CF_3$ | H | O |
| 1-33 | 3-nitro-5-trifluoromethyl-2-pyridyl | F | Cl | O | $CH_3$ | $CF_3$ | H | O |
| 1-34 | 3-chloro-5-trifluoromethyl-2-pyridyl | F | Cl | O | $CH_3$ | $CF_3$ | H | O |
| 1-35 | 3,5-dichloro-2-pyridyl | F | Cl | O | $CH_3$ | $CF_3$ | H | O |
| 1-36 | 3,5-dinitro-2-pyridyl | F | Cl | O | $CH_3$ | $CF_3$ | H | O |
| 1-37 | 4,6-bistrifluoromethyl-2-pyridyl | F | Cl | O | $CH_3$ | $CF_3$ | H | O |
| 1-38 | 6-chloro-4-cyano-2-pyridyl | F | Cl | O | $CH_3$ | $CF_3$ | H | O |
| 1-39 | 4,5-bistrifluoromethyl-2-pyridyl | F | Cl | O | $CH_3$ | $CF_3$ | H | O |
| 1-40 | 3,6-bistrifluoromethyl-2-pyridyl | F | Cl | O | $CH_3$ | $CF_3$ | H | O |
| 1-41 | 3,5,6-trichloro-4-trifluoromethyl-2-pyridyl | F | Cl | O | $CH_3$ | $CF_3$ | H | O |
| 1-42 | 3,4,5-trichloro-6-trifluoromethyl-2-pyridyl | F | Cl | O | $CH_3$ | $CF_3$ | H | O |
| 1-43 | 3,5-dichloro-4,6-difluoro-2-pyridyl | F | Cl | O | $CH_3$ | $CF_3$ | H | O |
| 1-44 | 4-bromo-3,5,6-trifluoro-2-pyridyl | F | Cl | O | $CH_3$ | $CF_3$ | H | O |
| 1-45 | 3,4,5,6-tetrachloro-2-pyridyl | F | Cl | O | $CH_3$ | $CF_3$ | H | O |
| 1-46 | 3-methyl-4-nitro-5-isothiazolyl | F | Cl | O | $CH_3$ | $CF_3$ | H | O |
| 1-47 | phenyl | F | Cl | O | $CH_3$ | $CF_3$ | H | O |
| 1-48 | 2-aminophenyl | F | Cl | O | $CH_3$ | $CF_3$ | H | O |
| 1-49 | 2-nitrophenyl | F | Cl | O | $CH_3$ | $CF_3$ | H | O |
| 1-50 | 4-nitro-2-trifluoromethylphenyl | F | Cl | O | $CH_3$ | $CF_3$ | H | O |
| 1-51 | 3-nitro-5-trifluoromethylphenyl | F | Cl | O | $CH_3$ | $CF_3$ | H | O |
| 1-52 | 2-trifluoromethylphenyl | F | Cl | O | $CH_3$ | $CF_3$ | H | O |
| 1-53 | 3-trifluoromethylphenyl | F | Cl | O | $CH_3$ | $CF_3$ | H | O |
| 1-54 | 4-(1-ethoxycarbonylethoxy)-phenyl | F | Cl | O | $CH_3$ | $CF_3$ | H | O |
| 1-55 | 2-chloro-6-nitrophenyl | F | Cl | O | $CH_3$ | $CF_3$ | H | O |
| 1-56 | 4-fluoro-6-nitrophenyl | F | Cl | O | $CH_3$ | $CF_3$ | H | O |

TABLE I-continued

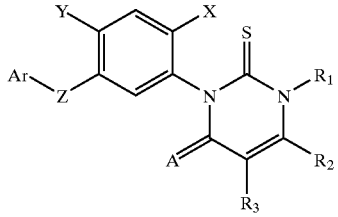

| No. | Ar | X | Y | Z | R₁ | R₂ | R₃ | A |
|---|---|---|---|---|---|---|---|---|
| 1-57 | 3-fluoro-6-nitrophenyl | F | Cl | O | CH₃ | CF₃ | H | O |
| 1-58 | 3-fluoro-2-nitrophenyl | F | Cl | O | CH₃ | CF₃ | H | O |
| 1-59 | 2-fluorophenyl | F | Cl | O | CH₃ | CF₃ | H | O |
| 1-60 | 3-fluorophenyl | F | Cl | O | CH₃ | CF₃ | H | O |
| 1-61 | 4-fluorophenyl | F | Cl | O | CH₃ | CF₃ | H | O |
| 1-62 | 2-chloro-4-nitrophenyl | F | Cl | O | CH₃ | CF₃ | H | O |
| 1-63 | 4-cyano-2,3,5,6-tetrafluoro-phenyl | F | Cl | O | CH₃ | CF₃ | H | O |
| 1-64 | 3-chloro-4,6-dinitrophenyl | F | Cl | O | CH₃ | CF₃ | H | O |
| 1-65 | 4-nitrophenyl | F | Cl | O | CH₃ | CF₃ | H | O |
| 1-66 | 2-cyanophenyl | F | Cl | O | CH₃ | CF₃ | H | O |
| 1-67 | 2-cyano-3-fluorophenyl | F | Cl | O | CH₃ | CF₃ | H | O |
| 1-68 | phenyl | F | Cl | O | CH₃ | CF₃ | H | S |
| 1-69 | phenyl | F | CN | O | CH₃ | CF₃ | H | O |
| 1-70 | 2-hydroxyphenyl | F | CN | O | CH₃ | CF₃ | H | O |
| 1-71 | 2-methoxyphenyl | F | CN | O | CH₃ | CF₃ | H | O |
| 1-72 | 4-methoxyphenyl | F | CN | O | CH₃ | CF₃ | H | O |
| 1-73 | 2-R-phenyl R = 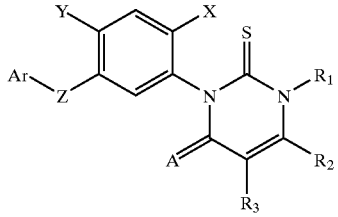 | F | CN | O | CH₃ | CF₃ | H | O |
| 1-74 | 2-R-phenyl R = 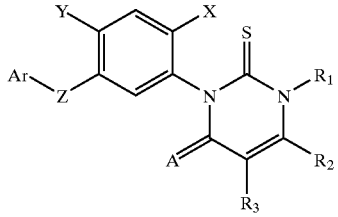 | F | CN | O | CH₃ | CF₃ | H | O |
| 1-75 | 1-naphthyl | F | Cl | O | CH₃ | CF₃ | H | O |
| 1-76 | 2-naphthyl | F | Cl | O | CH₃ | CF₃ | H | O |

TABLE II

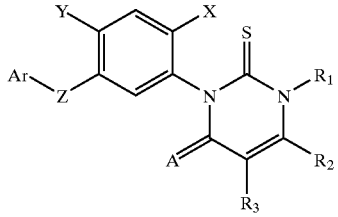

| No. | Ar | X | Y | Z | R₁ | A |
|---|---|---|---|---|---|---|
| 2-1 | 2-pyrimidyl | F | Cl | O | CH₃ | O |
| 2-2 | 4-chloro-2-pyrimidyl | F | Cl | O | CH₃ | O |
| 2-3 | 4,6-dimethoxy-2-pyrimidyl | F | Cl | O | CH₃ | O |
| 2-4 | 6-chloro-4-pyridazinyl | F | Cl | O | CH₃ | O |
| 2-5 | 6-chloro-3-pyridazinyl | F | Cl | O | CH₃ | O |
| 2-6 | 2-pyridyl | F | Cl | O | CH₃ | O |
| 2-7 | 3-nitro-2-pyridyl | F | Cl | O | CH₃ | O |
| 2-8 | 6-fluoro-2-pyridyl | F | Cl | O | CH₃ | O |
| 2-9 | 6-chloro-2-pyridyl | F | Cl | O | CH₃ | O |
| 2-10 | 3-trifluoromethyl-2-pyridyl | F | Cl | O | CH₃ | O |
| 2-11 | 3-cyano-2-pyridyl | F | Cl | O | CH₃ | O |
| 2-12 | 3-nitro-2-pyridyl | F | Cl | O | CH₃ | O |
| 2-13 | 5-trifluoromethyl-2-pyridyl | F | Cl | O | CH₃ | O |
| 2-14 | 3-chloro-2-pyridyl | F | Cl | O | CH₃ | O |
| 2-15 | 3-chloro-5-trifluoromethyl-2-pyridyl | F | Cl | O | CH₃ | O |
| 2-16 | phenyl | F | Cl | O | CH₃ | O |
| 2-17 | 2-nitrophenyl | F | Cl | O | CH₃ | O |
| 2-18 | 2-aminophenyl | F | Cl | O | CH₃ | O |
| 2-19 | 2-trifluoromethylphenyl | F | Cl | O | CH₃ | O |
| 2-20 | 2-fluorophenyl | F | Cl | O | CH₃ | O |
| 2-21 | 4-nitrophenyl | F | Cl | O | CH₃ | O |
| 2-22 | 2-cyanophenyl | F | Cl | O | CH₃ | O |
| 2-23 | phenyl | F | CN | O | CH₃ | O |
| 2-24 | 1-naphthyl | F | Cl | O | CH₃ | O |
| 2-25 | 2-naphthyl | F | Cl | O | CH₃ | O |

TABLE III

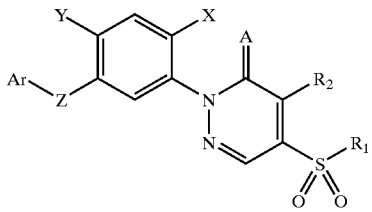

| No. | Ar | X | Y | Z | R₁ | R₂ | A |
|---|---|---|---|---|---|---|---|
| 3-1 | 2-pyrimidyl | F | Cl | O | CH₃ | NH₂ | O |
| 3-2 | 4-chloro-2-pyrimidyl | F | Cl | O | CH₃ | NH₂ | O |
| 3-3 | 4,6-dimethoxy-2-pyrimidyl | F | Cl | O | CH₃ | NH₂ | O |
| 3-4 | 6-chloro-4-pyridazinyl | F | Cl | O | CH₃ | NH₂ | O |
| 3-5 | 6-chloro-3-pyridazinyl | F | Cl | O | CH₃ | NH₂ | O |
| 3-6 | 2-pyridyl | F | Cl | O | CH₃ | NH₂ | O |
| 3-7 | 3-nitro-2-pyridyl | F | Cl | O | CH₃ | NH₂ | O |
| 3-8 | 6-fluoro-2-pyridyl | F | Cl | O | CH₃ | NH₂ | O |
| 3-9 | 6-chloro-2-pyridyl | F | Cl | O | CH₃ | NH₂ | O |
| 3-10 | 3-trifluoromethyl-2-pyridyl | F | Cl | O | CH₃ | NH₂ | O |
| 3-11 | 3-cyano-2-pyridyl | F | Cl | O | CH₃ | NH₂ | O |
| 3-12 | 3-nitro-2-pyridyl | F | Cl | O | CH₃ | NH₂ | O |
| 3-13 | 5-trifluoromethyl-2-pyridyl | F | Cl | O | CH₃ | NH₂ | O |
| 3-14 | 3-chloro-2-pyridyl | F | Cl | O | CH₃ | NH₂ | O |
| 3-15 | 3-chloro-5-trifluoro-methyl-2-pyridyl | F | Cl | O | CH₃ | NH₂ | O |
| 3-16 | phenyl | F | Cl | O | CH₃ | NH₂ | O |
| 3-17 | 2-nitrophenyl | F | Cl | O | CH₃ | NH₂ | O |
| 3-18 | 2-trifluoromethylphenyl | F | Cl | O | CH₃ | NH₂ | O |
| 3-19 | 2-fluorophenyl | F | Cl | O | CH₃ | NH₂ | O |
| 3-20 | 4-nitrophenyl | F | Cl | O | CH₃ | NH₂ | O |
| 3-21 | 2-cyanophenyl | F | Cl | O | CH₃ | NH₂ | O |
| 3-22 | phenyl | F | CN | O | CH₃ | NH₂ | O |
| 3-23 | 1-naphthyl | F | Cl | O | CH₃ | NH₂ | O |
| 3-24 | 2-naphthyl | F | Cl | O | CH₃ | NH₂ | O |

TABLE IV

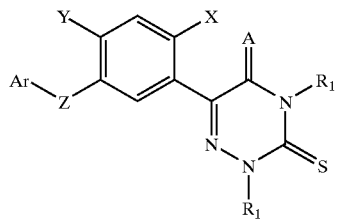

| No. | Ar | X | Y | Z | R₁ | A |
|---|---|---|---|---|---|---|
| 4-1 | 2-pyrimidyl | F | Cl | O | CH₃ | O |
| 4-2 | 4-chloro-2-pyrimidyl | F | Cl | O | CH₃ | O |
| 4-3 | 4,6-dimethoxy-2-pyrimidyl | F | Cl | O | CH₃ | O |
| 4-4 | 6-chloro-4-pyridazinyl | F | Cl | O | CH₃ | O |
| 4-5 | 6-chloro-3-pyridazinyl | F | Cl | O | CH₃ | O |
| 4-6 | 2-pyridyl | F | Cl | O | CH₃ | O |
| 4-7 | 3-nitro-2-pyridyl | F | Cl | O | CH₃ | O |
| 4-8 | 6-fluoro-2-pyridyl | F | Cl | O | CH₃ | O |
| 4-9 | 6-chloro-2-pyridyl | F | Cl | O | CH₃ | O |
| 4-10 | 3-trifluoromethyl-2-pyridyl | F | Cl | O | CH₃ | O |
| 4-11 | 3-cyano-2-pyridyl | F | Cl | O | CH₃ | O |
| 4-12 | 3-nitro-2-pyridyl | F | Cl | O | CH₃ | O |
| 4-13 | 5-trifluoromethyl-2-pyridyl | F | Cl | O | CH₃ | O |
| 4-14 | 3-chloro-2-pyridyl | F | Cl | O | CH₃ | O |
| 4-15 | 3-chloro-5-trifluoromethyl-2-pyridyl | F | Cl | O | CH₃ | O |
| 4-16 | phenyl | F | Cl | O | CH₃ | O |
| 4-17 | 2-nitrophenyl | F | Cl | O | CH₃ | O |
| 4-18 | 2-trifluoromethylphenyl | F | Cl | O | CH₃ | O |
| 4-19 | 2-fluorophenyl | F | Cl | O | CH₃ | O |
| 4-20 | 4-nitrophenyl | F | Cl | O | CH₃ | O |
| 4-21 | 2-cyanophenyl | F | Cl | O | CH₃ | O |
| 4-22 | phenyl | F | CN | O | CH₃ | O |

TABLE IV-continued

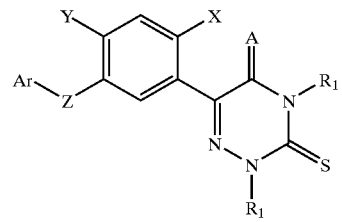

| No. | Ar | X | Y | Z | R₁ | A |
|---|---|---|---|---|---|---|
| 4-23 | 1-naphthyl | F | Cl | O | CH₃ | O |
| 4-24 | 2-naphthyl | F | Cl | O | CH₃ | O |

TABLE V

| No. | Ar | X | Y | Z | R₁ | R₂ | R₃ |
|---|---|---|---|---|---|---|---|
| 5-1 | 2-pyrimidyl | F | Cl | O | CHF₂ | Cl | CH₃ |
| 5-2 | 4-chloro-2-pyrimidyl | F | Cl | O | CHF₂ | Cl | CH₃ |
| 5-3 | 4,6-dimethoxy-2-pyrimidyl | F | Cl | O | CHF₂ | Cl | CH₃ |
| 5-4 | 6-chloro-4-pyridazinyl | F | Cl | O | CHF₂ | Cl | CH₃ |
| 5-5 | 6-chloro-3-pyridazinyl | F | Cl | O | CHF₂ | Cl | CH₃ |
| 5-6 | 2-pyridyl | F | Cl | O | CHF₂ | Cl | CH₃ |
| 5-7 | 3-nitro-2-pyridyl | F | Cl | O | CHF₂ | Cl | CH₃ |
| 5-8 | 6-fluoro-2-pyridyl | F | Cl | O | CHF₂ | Cl | CH₃ |
| 5-9 | 6-chloro-2-pyridyl | F | Cl | O | CHF₂ | Cl | CH₃ |
| 5-10 | 3-trifluoromethyl-2-pyridyl | F | Cl | O | CHF₂ | Cl | CH₃ |
| 5-11 | 3-cyano-2-pyridyl | F | Cl | O | CHF₂ | Cl | CH₃ |
| 5-12 | 3-nitro-2-pyridyl | F | Cl | O | CHF₂ | Cl | CH₃ |
| 5-13 | 5-trifluoromethyl-2-pyridyl | F | Cl | O | CHF₂ | Cl | CH₃ |
| 5-14 | 3-chloro-2-pyridyl | F | Cl | O | CHF₂ | Cl | CH₃ |
| 5-15 | 3-chloro-5-trifluoro-methyl-2-pyridyl | F | Cl | O | CHF₂ | Cl | CH₃ |
| 5-16 | 1-naphthyl | F | Cl | O | CHF₂ | Cl | CH₃ |
| 5-17 | 2-naphthyl | F | Cl | O | CHF₂ | Cl | CH₃ |

TABLE VI

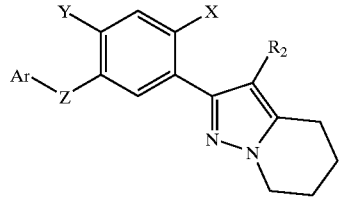

| No. | Ar | X | Y | Z | R₂ |
|---|---|---|---|---|---|
| 6-1 | 2-pyrimidyl | F | Cl | O | Cl |
| 6-2 | 2-pyrimidyl | F | Cl | O | Br |
| 6-3 | 4-chloro-2-pyrimidyl | F | Cl | O | Cl |
| 6-4 | 4,6-dimethoxy-2-pyrimidyl | F | Cl | O | Cl |
| 6-5 | 6-chloro-4-pyridazinyl | F | Cl | O | Cl |
| 6-6 | 6-chloro-3-pyridazinyl | F | Cl | O | Cl |
| 6-7 | 2-pyridyl | F | Cl | O | Cl |
| 6-8 | 3-nitro-2-pyridyl | F | Cl | O | Cl |
| 6-9 | 6-fluoro-2-pyridyl | F | Cl | O | Cl |
| 6-10 | 6-chloro-2-pyridyl | F | Cl | O | Cl |
| 6-11 | 3-trifluoromethyl-2-pyridyl | F | Cl | O | Cl |
| 6-12 | 3-cyano-2-pyridyl | F | Cl | O | Cl |
| 6-13 | 3-nitro-2-pyridyl | F | Cl | O | Cl |
| 6-14 | 5-trifluoromethyl-2-pyridyl | F | Cl | O | Cl |
| 6-15 | 3-chloro-2-pyridyl | F | Cl | O | Cl |
| 6-16 | 3-chloro-5-trifluoromethyl-2-pyridyl | F | Cl | O | Cl |
| 6-17 | 2-pyrimidyl | F | Cl | O | CN |
| 6-18 | phenyl | F | Cl | O | Cl |
| 6-19 | 2-nitrophenyl | F | Cl | O | Cl |
| 6-20 | 2-trifluoromethylphenyl | F | Cl | O | Cl |

TABLE VI-continued

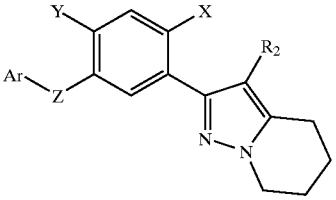

| No. | Ar | X | Y | Z | R$_2$ |
|---|---|---|---|---|---|
| 6-21 | 2-fluorophenyl | F | Cl | O | Cl |
| 6-22 | 4-nitrophenyl | F | Cl | O | Cl |
| 6-23 | 2-cyanophenyl | F | Cl | O | Cl |
| 6-24 | phenyl | F | CN | O | Cl |
| 6-25 | 1-naphthyl | F | Cl | O | Cl |
| 6-26 | 2-naphthyl | F | Cl | O | Cl |

Table VII lists some of the characterization data for a few representative compounds of this invention.

TABLE VII

$^1$H NMR data

| No | NMR (CDCl$_3$, 300 MHz) ppm |
|---|---|
| 1-1 | 3.91 (3 H, m), 6.60 (1 H, s), 7.08 (1 H, t, J = 4.8 Hz), 7.17 (1 H, d, J = 6.7 Hz), 7.42 (1 H, d, J = 8.9 Hz), 8.58 (2 H, d, J = 4.8 Hz). |
| 1-9 | 3.91 (3 H, m), 6.60 (1 H, s), 7.18 (1 H, d, J = 6.7 Hz), 7.21 (1 H, dd, J = 4.8, 7.9 Hz), 7.42 (1 H, d, J = 8.8 Hz), 8.34 (1 H, dd, J = 1.8, 4.8 Hz), 8.41 (1 H, dd, J = 1.8, 7.9 Hz). |
| 1-15 | 3.90 (3 H, m), 6.59 (1 H, s), 7.11 (1 H, m), 7.16 (1H, d, J = 6.8 Hz), 7.41 (1 H, d, J = 8.9 Hz), 8.00 (1 H, m), 8.27 (1 H, m). |
| 1-47 | 3.88 (3 H, m), 6.55 (1 H, s), 6.84 (1 H, d, J = 6.7 Hz), 7.0 (2 H, m), 7.12 (1 H, m), 7.3–7.41 (2 H, m). |
| 1-48 | 3.86 (3 H, m), 6.54 (1 H, s), 6.70 (1 H, m), 6.73 (1 H, d, J = 6.6 Hz), 6.70–6.90 (2 H, m), 6.98 (1 H, m), 7.38 (1 H, d, J = 8.8 Hz). |
| 1-49 | 3.89 (3 H, m), 6.57 (1 H, s), 6.93 (1 H, m), 6.99 (1 H, d, J = 6.5 Hz), 7.22 (1 H, m), 7.43 (1 H, d, J = 8.8 Hz), 7.52 (1 H, m), 7.98 (1 H, m). |
| 1-66 | 3.90 (3 H, m), 6.59 (1 H, s), 6.78 (1 H, m), 7.07 (1 H, d, J = 6.6 Hz), 7.16 (1 H, m), 7.44 (1 H, d, J = 8.8 Hz), 7.49 (1 H, m), 7.67 (1H, m). |
| 1-69 | 3.86 (3 H, m), 6.54 (1 H, s), 6.75 (1 H, d, J = 5.9 Hz), 7.11 (2 H, m), 7.21 (1 H, m), 7.41 (2 H, m), 7.54 (1 H, d, J = 8.4 Hz). |
| 1-70 | 3.86 (3 H, m), 5.60 (1 H, br s), 6.54 (1 H, s), 6.77 (1 H, d, J = 5.8 Hz), 6.90 (1 H, m), 6.95–7.05 (2 H, m), 7.12 (1 H, m), 7.54 (1 H, d, J = 8.3 Hz). |
| 1-71 | 3.75 (3 H, s), 3.84 (3 H. m), 6.50 (1 H, m), 6.52 (1 H, s), 6.90–7.00 (2 H, m), 7.14–7.25 (2 H, m), 7.50 (1 H, d, J = 8.4 Hz). |
| 1-72 | 3.80 (3 H, s), 3.85 (3 H. m), 6.53 (1 H, s), 6.65 (1 H, d, J = 5.9 Hz), 6.91 (2 H, m), 7.05 (2 H, m), 7.51 (1 H, d, J = 8.4 Hz). |
| 1-73 | 1.23 (3 H, m), 3.27 (1 H, m), 3.45 (1 H, m), 3.89 (3 H, s), 4.18 (2 H, m), 4.73 (1 H, m), 6.57 (1 H, s), 6.76 (1 H, m), 6.88 (1 H, m), 7.06 (1 H, m), 7.20–7.30 (2 H, m), 7.42 (1 H, d, J = 8.8 Hz). |
| 1-74 | 1.50 (3 H, s), 1.53 (3 H, s), 3.84 (3 H, m), 4.62 (2 H, m), 5.10–5.30 (2 H, m), 5.75–5.90 (1 H, m), 6.50 (1 H, s), 6.61 (1 H, d, J = 5.8 Hz), 6.87 (1 H, m), 7.01 (1 H, m), 7.12 (1 H, m), 7.19 (1 H, m), 7.49 (1 H, d, J = 8.4 Hz). |
| 2-1 | 3.78 (6 H, s), 7.09 (1 H, t, J = 4.7 Hz), 7.29 (1 H, d, J = 6.7 Hz), 7.42 (1 H, d, J = 9.0 Hz), 8.57 (2 H, d, 4.7 Hz). |
| 2-16 | 3.74 (6 H, s), 6.90 (1 H, d, J = 6.7 Hz), 7.02 (2 H, m), 7.15 (1 H, m), 7.32–7.43 (3 H, m). |
| 2-17 | 3.75 (6 H, s), 6.95 (1 H, m), 7.08 (1 H, d, J = 6.6 Hz), 7.26 (1 H, m), 7.45 (1 H, d, J = 8.8 Hz), 7.55 (1 H, m), 7.99 (1 H, m). |
| 2-18 | 3.73 (6 H, s), 6.71 (1 H, m), 6.76–6.89 (3 H, m), 7.01 (1 H, m), 7.39 (1 H, d, J = 8.9 Hz). |

TABLE VII-continued

$^1$H NMR data

| No | NMR (CDCl$_3$, 300 MHz) ppm |
|---|---|
| 4-1 | 3.76 (3 H, s), 4.05 (3 H, s), 7.09 (1 H, t, J = 4.8 Hz), 7.35 (1 H, d, J = 8.7 Hz), 7.53 (1 H, d, J = 6.49 Hz), 8.58 (2 H, d, J = 4.8 Hz). |
| 5-1 | 4.18 (3 H, s), 6.73 (1 H, t, J = 54.6 Hz), 7.09 (1 H, t, J = 4.8 Hz), 7.37 (1 H, d, J = 9.2 Hz), 7.50 (1 H, d, J = 6.6 Hz), 8.57 (2 H, d, J = 4.8 Hz). |
| 6-1 | 1.91 (2 H, m), 2.07 (2 H, m), 2.76 (2 H, t, J = 6.3 Hz), 4.16 (2 H, t, J = 6.0 Hz), 7.07 (1 H, t, J = 4.7 Hz), 7.33 (1 H, d, J = 9.3 Hz), 7.52 (1 H, d, J = 6.6 Hz), 8.56 (2 H, d, J = 4.7 Hz). |
| 6-2 | 1.91 (2 H, m), 2.06 (2 H, m), 2.74 (2 H, t, J = 6.3 Hz), 4.17 (2 H, d, J = 5.8 Hz), 7.07 (1 H, t, J = 4.7 Hz), 7.32 (1 H, d, J = 9.2 Hz), 7.50 (1 H, d, J = 6.5 Hz), 8.56 (2 H, d, J = 4.7 Hz). |
| 6-17 | 1.97 (2 H, m), 2.11 (2 H, m), 2.98 (2 H, t, J = 6.2 Hz), 4.19 (2 H, t, J = 5.9 Hz), 7.09 (1 H, t, J = 4.7 Hz), 7.37 (1 H, d, J = 9.4 Hz), 7.64 (1 H, d, J = 6.6 Hz), 8.57 (2 H, d, J = 4.7 Hz). |

Herbicidal Activity

The compounds of the present invention exhibit excellent herbicidal effects when used as an active ingredient of a herbicide. The herbicide can be used for a wide range of applications, for example on crop lands such as paddy fields, upland farms, orchards and mulberry fields, and non-crop lands such as forests, farm roads, playgrounds, and factory sites. They can also be used in a wide range of application, as plant growth regulator for defoliating crop plants such as cotton, potato and the like, and causing uniform boll opening, or desiccating these crop vines, or crop foliage and for controlling the growth of some plants. The application method may be suitably selected for soil treatment application and foliar application.

The compounds of the present invention are capable of controlling noxious weeds including grass (gramineae) such as barnyardgrass (*Echinochloa crus-galli*), large crabgrass (*Digitaria sanguinalis*), green foxtail (*Setaria viridis*), goosegrass (*Eleusine indica* L.), wild oat (*Avena fatua* L.), Johnsongrass (*Sorghum halepense*), quackgrass (*Agropyron repens*), alexandergrass (*Brachiaria plantaginea*), paragrass (*Panicum purpurascen*), sprangletop (*Leptochloa chinensis*) and red sprangletop (*Leptochloa panicea*); sedges (or Cyperaceae) such as rice flatsedge (*Cyperus iria* L.), purple nutsedge (*Cyperus rotundus* L.), Japanese bulrush (*Scirpus juncoides*), flatsedge (*Cyperus serotinus*), small-flower umbrellaplant (*Cyperus difformis*), slender spikerush (*Eleocharis acicularis*), and water chestnut (*Eleocharis kuroguwai*); alismataceae such as Japanese ribbon wapato (*Sagittaria pygmaea*), arrow-head (*Sagittaria trifolia*) and narrowleaf waterplantain (*Alisma canaliculatum*); ponted-eriaceae such as monochoria (*Monochoria vaginalis*) and monochoria species (*Monochoria korsakowii*); scrophulariaceae such as false pimpernel (*Lindernia pyxidaria*) and abunome (*Dopatrium Junceum*); lythraceae such as toothcup (*Rotala indica*) and red stem (*Ammannia multiflora*); and broadleaves such as redroot pigweed (*Amaranthus retroflexus*), velvetleaf (*Abutilon theophrasti*), morningglory (*Ipomoea hederacea*), lambsquarters (*Chenopodium album*), prickly sida (*Sida spinosa* L.), common purslane (*Portulaca oleracea* L.), slender amaranth (*Amaranthus viridis* L.), sicklepod (*Cassia obtusifolia*), black nightshade (*Solanum nigrum* L.), pale smartweed (*Polygonum lapathifolium* L.), common chickweed (*Stellaria media* L.), common cocklebur (*Xanthium strumarium* L.), flexuous bittercress (*Cardamine flexuosa* WITH.), henbit (*Lamium*

*amplexicaule* L.) and threeseeded copperleaf (*Acalypha australis* L.). Accordingly, it is useful for controlling noxious weeds non-selectively or selectively in the cultivation of a crop plant such as corn (*Zea mays* L.), soybean (*Glycine max* Merr.), cotton (*Gossypium* spp.), wheat (*Triticum* spp.), rice (*Oryza sativa* L.), barley (*Hordeum vulgare* L.), oat (*Avena sativa* L.), sorgo (*Sorghum bicolor* Moench), rape (*Brassica napus* L.), sunflower (*Helianthus annuus* L.), sugar beet (*Beta vulgaris* L.), sugar cane (*Saccharum officinarum* L.), Japanese lawngrass (*Zoysia Japonica stend*), peanut (*Arachis hypogaea* L.) or flax (*Linum usitatissimum* L.).

For the desired use such as herbicides, the active ingredients of this invention are formulated into compositions for the desired use by mixing effectively active amounts with inert ingredients known to the art to facilitate either the suspension, dissolution or emulsification of the active ingredient for the desired use. The type of formulation prepared recognizes the facts that formulation, crop and use pattern all can influence the activity and utility of the active ingredient in a particular use. Thus for agricultural use the present compounds may be formulated as water dispersible granules, granules for direct application to soils, water soluble concentrates, wettable powders, dusts, solutions, emulsifiable concentrates (EC), microemulsion, suspoemulsion, invert emulsion or other types of formulations, depending on the desired weed targets, crops and application methods.

These formulations may be applied to the target area (where suppression of unwanted vegetation is the objective) as dusts, granules or water or solvent diluted sprays. These formulation may contain as little as 0.1% to as much as 97% active ingredient by weight.

Dusts are admixtures of the active ingredient with finely ground materials such as clays (some examples include kaolin and montmorillonite clays), talc, granite dust or other organic or inorganic solids which act as dispersants and carriers for the active ingredient; these finely ground materials have an average particle size of less than 50 microns. A typical dust formulation will contain 1% active ingredient and 99% carrier.

Wettable powders are composed of finely ground particles which disperse rapidly in water or other spray carriers. Typical carriers include kaolin clays, Fullers earth, silicas and other absorbent, wettable inorganic materials. Wettable powders can be prepared to contain from 1 to 90% active ingredient, depending on the desired use pattern and the absorbability of the carrier. Wettable powders typically contain wetting or dispersing agents to assist dispersion in water or other carriers.

Water dispersible granules are granulated solids that freely disperse when mixed in water. This formulation typically consists of the active ingredient (0.1% to 95% active ingredient), a wetting agent (1–15% by weight), a dispersing agent (1 to 15% by weight) and an inert carrier (1–95% by weight). Water dispersible granules can be formed by mixing the ingredients intimately then adding a small amount of water on a rotating disc (said mechanism is commercially available) and collecting the agglomerated granules. Alternatively, the mixture of ingredients may be mixed with an optimal amount of liquid (water or other liquid) and passed through an extruder (said mechanism is commercially available) equipped with passages which allow for the formation of small extruded granules. Alternatively, the mixture of ingredients can be granulated using a high speed mixer (said mechanism is commercially available) by adding a small amount of liquid and mixing at high speeds to affect agglomeration. Alternatively, the mixture of ingredients can be dispersed in water and dried by spraying the dispersion through a heated nozzle in a process known as spray drying (spray drying equipment is commercially available). After granulation the moisture content of granules is adjusted to an optimal level (generally less than 5%) and the product is sized to the desired mesh size.

Granules are granulated solids that do not disperse readily in water, but instead maintain their physical structure when applied to the soil using a dry granule applicator. These granulated solids may be made of clay, vegetable material such as corn cob grits, agglomerated silicas or other agglomerated organic or inorganic materials or compounds such as calcium sulfate. The formulation typically consists of the active ingredient (1 to 20%) dispersed on or absorbed into the granule. The granule may be produced by intimately mixing the active ingredient with the granules with or without a sticking agent to facilitate adhesion of the active ingredient to the granule surface, or by dissolving the active ingredient in a solvent, spraying the dissolved active ingredient and solvent onto the granule then drying to remove the solvent. Granular formulations are useful where in-furrow or banded application is desired.

Emulsifiable concentrates (EC) are homogeneous liquids composed of a solvent or mixture of solvents such as xylenes, heavy aromatic naphthas, isophorone or other proprietary commercial compositions derived from petroleum distillates, the active ingredient and an emulsifying agent or agents. For herbicidal use, the EC is added to water (or other spray carrier) and applied as a spray to the target area. The composition of an EC formulation can contain 0.1% to 95% active ingredient, 5 to 95% solvent or solvent mixture and 1 to 20% emulsifying agent or mixture of emulsifying agents.

Suspension concentrate (also known as flowable) formulations are liquid formulations consisting of a finely ground suspension of the active ingredient in a carrier, typically water or a non-aqueous carrier such as an oil. Suspension concentrates typically contain the active ingredient (5 to 50% by weight), carrier, wetting agent, dispersing agent, anti-freeze, viscosity modifiers and pH modifiers. For application, suspension concentrates are typically diluted with water and sprayed on the target area.

Solution concentrates are solutions of the active ingredient (1 to 70%) in solvents which have sufficient solvency to dissolve the desired amount of active ingredient. Because they are simple solutions without other inert ingredients such as wetting agents, additional additives are usually added to the spray tank mix before spraying to facilitate proper application.

Microemulsions are solutions consisting of the active ingredient (1 to 30%) dissolved in a surfactant or emulsifier, without any additional solvents. There are no additional solvents added to this formulation. Microemulsions are particularly useful when a low odor formulation is required such as in residential turfgrass applications.

Suspoemulsions are combinations of two active ingredients. One active ingredient is made as a suspension concentrate (1–50% active ingredient) and the second active is made as a emulsifiable concentrate (0.1 to 20%). A reason for making this kind of formulation is the inability to make an EC formulation of the first ingredient due to poor solubility in organic solvents. The suspoemulsion formulation allows for the combination of the two active ingredients to be packaged in one container, thereby minimizing packaging waste and giving greater convenience to the product user.

The compounds of this invention may be formulated or applied with insecticides, fungicides, acaricides, nematicides, fertilizers, plant growth regulators or other agricultural chemicals. Certain tank mix additives, such as spreader stickers, penetration aids, wetting agents, surfactants, emulsifiers, humectants and UV protectants may be added in amounts of 0.01% to 5% to enhance the biological activity, stability, wetting, spreading on foliage or uptake of the active ingredients on the target area or to improve the suspensibility, dispersion, redispersion, emulsifiability, UV stability or other physical or physicochemical property of the active ingredient in the spray tank, spray system or target area.

The compositions of the present invention may be used in admixture with or in combination with other agricultural chemicals, fertilizers, adjuvants, surfactants, emulsifiers, oils, polymers or phytotoxicity-reducing agents such as herbicide safeners. In such a case, they may exhibit even better effects or activities. As other agricultural chemicals, herbicides, fungicides, antibiotics, plant hormones, plant growth regulators, insecticides, or acaricides may, for example, be mentioned. Especially with herbicidal compositions having the compounds of the present invention used in admixture with or in combination with one or more active ingredients of other herbicides, it is possible to improve the herbicidal activities, the range of application time(s) and the range of applicable weed types. Further, the compounds of the present invention and an active ingredient of another herbicide may be separately formulated so they may be mixed for use at the time of application, or both may be formulated together. The present invention covers such herbicidal compositions.

The blend ratio of the compounds of the present invention with the active ingredient of other herbicides can not generally be defined, since it varies depending on the time and method of application, weather conditions, soil type and type of formulation. However one active ingredient of other herbicide may be incorporated usually in an amount of 0.01 to 100 parts by weight, per one part by weight of the compounds of the present invention. Further, the total dose of all of the active ingredients is usually from 1 to 10000 g/ha, preferably from 5 to 500 g/ha. The present invention covers such herbicidal compositions.

As the active ingredients of other herbicides, the following (common name) may be mentioned. The compositions having the compounds of the present invention used in combination with other herbicides or plant growth regulators, may occasionally exhibit a synergistic effect.

1. Those that are believed to exhibit herbicidal effects by disturbing auxin activities of plants, including a phenoxy acetic acid type such as 2,4-D, 2,4-DB, 2,4-DP, MCPA, MCPP, MCPB or naproanilide (including the free acids, esters or salts thereof), an aromatic carboxylic type such as 2,3,6 TBA, dicamba, dichlobenil, a pyridine type such as picloram (including free acids and salts thereof), triclopyr or clopyralid and others such as naptalam, benazolin, quinclorac, quinmerac diflufenzopyr (BAS 654H) or thiazopyr.
2. Those that are believed to exhibit herbicidal effects by inhibiting photosynthesis of plants including a urea type such as diuron, linuron, isoproturon, chlorotoluron, metobenzuron, tebuthiuron or fluometuron, a triazine type such as simazine, atrazine, cyanazine, terbuthylazine, atraton, hexazinone, metribuzin, simetryn, ametryn, prometryn, dimethametryn triaziflam or propazine, a uracil type such as bromacil, terbacil or lenacil, an anilide type such as propanil or cypromid, a carbamate type such as desmedipham or phenmedipham, a hydroxybenzonitrile type such as bromoxynil or ioxynil, and others such as pyridate, bentazon, methazole or amicarbazone.
3. A quaternary ammonium salt type such as paraquat, diquat or difenzoquat, which is believed to be converted to free radicals by itself to form active oxygen in the plant and thus to exhibit quick herbicidal effects.
4. Those which are believed to exhibit herbicidal effects by inhibiting chlorophyll biosynthesis in plants and abnormally accumulating a photsensitizing peroxide substance in the plant body, including a diphenyl ether type such as nitrofen, lactofen, acifluorfen-sodium, oxyfluorfen, fomesafen, bifenox, or chlomethoxyfen, a cyclic imide type such as chlorphthalim, flumioxazin, cinidon-ethyl, or flumiclorac-pentyl, and others such as oxadiazon, sulfentrazone, thidiazimin, azafenidin, carfentrazone, isopropazole, fluthiacet-methyl, pentoxazone, pyraflufen-ethyl, oxadiargyl, azafenidin, benzfendizone, cinidon-ethyl or fluazolate.
5. Those which are believed to exhibit herbicidal effects characterized by whitening activities by inhibiting chromogenesis of plants such as carotenoids including a pyridazinone type such as norflurazon, chloridazon or metflurazon, a pyrazol type such as pyrazolate, pyrazoxyfen or benzofenap, and others such as fluridone, fluramone, diflufencam, methoxyphenone, clomazone, amitrole, sulcotrione, mesotrione, isoxaflutole, isoxachlortole, picolinofen or beflubutamid.
6. Those which exhibit herbicidal effects specifically to gramineous plants including an aryloxyphenoxypropionic acid type (either as a mixture of isomers or as a resolved isomer) such as diclofop-methyl, pyrifenop-sodium, fluazifop butyl or fluazifop-p-butyl, haloxyfop-methyl, quizalofop p-ethyl, quizalafop p-tefuryl, fenoxaprop ethyl or fenoxaprop-p-ethyl, flamprop-M-methyl or flamprop-m-isopropyl or cyhalofop-butyl and a cyclohexanedione type such as alloxydim-sodium, sethoxydim, clethodim, tepraloxydim, tralkoxydim butroxydium orclefoxydim (BAS625H).
7. Those which are believed to exhibit herbicidal effects by inhibiting amino acid biosynthesis of plants, including a sulfonylurea type such as chlorimuron-ethyl, nicosulfuron, metsulfuron-methyl, triasulfuron, primisulfuron, tribenuron-methyl, chlorosulfuron, bensulfuron-methyl, sulfometuron-methyl, prosulfuron, halosulfuron or halosulfuron-methyl, thifensulfuron-methyl, rimsulfuron, azimsulfuron, flazasulfuron, imazosulfuron, cyclosulfamuron, flupyrsulfuron, iodosulfuron, ethoxysulfuron, sulfosulfuron, oxasulfuron, cinosulfuron, pyrazosulfuron, ethametsulfuron, tritosulfuron, foramsulfuron or trifloxysulfulon, a triazolopyrimidinesulfonamide type such as flumetsulam, metosulam, chloransulam, chloransulam-methyl, diclosulam, florasulam or penoxsulam, an imidazolinone type such as imazapyr, imazethapyr, imazaquin, imazamox, imazameth, imazamethabenz methyl, a pyrimidinesalicylic acid type such as pyrthiobac-sodium, bispyribac-sodium, pyriminobac-methyl, pyribenzoxim (LGC-40863) or pyriftalid, a sulfonylaminocarbonyl triazolinone type such as flucarbazone or procarbazone-sodium, and others such as glyphosate, glyphosate-ammonium, glyphosate-isopropylamine or sulfosate.
8. Those which are believed to exhibit herbicidal effects by interfering with the normal metabolism of inorganic nitrogen assimilation such as glufosinate, glufosinate-ammonium, phosphinothricin or bialophos.
9. Those which are believed to exhibit herbicidal effects by inhibiting cell division of plant cells, including a dinitroaniline type such as trifluralin, oryzalin, nitralin, pendamethalin, ethafluralin, benefin and prodiamine, an amide type such as bensulide, napronamide, and pronamide, a carbamate type such as propham, chlorpropham, barban, and asulam, an organophosphorous type such as amiprofos-methyl or butamifos and others such as DCPA and dithiopyr.

10. Those which are believed to exhibit herbicidal effects by inhibiting protein synthesis of plant cells, including a chloroacetanilide type such as alachlor, metolachor (including combinations with safeners such as benoxacor, or resolved isomeric mixtures of metolachlor including safeners such as benoxacor) propachlor, acetochlor (including combinations with herbicide safeners such as dichlormid or MON 4660 or resolved isomeric mixtures of acetochlor containing safeners such as dichlormid or MON 4660), propisochlor or dimethenamid or an oxyacetamide type such as flufenacet.

11. Those in which the mode of action causing the herbicidal effects are not well understood including the dithiocarbamates such as thiobencarb, EPTC, diallate, triallate, molinate, pebulate, cycloate, butylate, vernolate or pro-sulfocarb and miscellaneous herbicides such as MSMA, DSMA, endothall, ethofumesate, sodium chlorate, pelargonic acid, fosamine or tridiphane.

12. Those which are believed to exhibit effects of plant growth regulators, including organic phosphorous type compounds such as ethephon, tribufos; urea type compounds such as thiadiazuron; tetraoxides type compounds such as dimethapin and 1-aminomethanamide dihydrogen tetraoxosulfate; inorganic salts such as sodium chlorate; and mineral acids such as sulfonic acid.

A few formulation examples of the present invention are given as follows.

| Ingredient Trade Name | Chemical Name | Supplier | Function | % wt./wt. |
|---|---|---|---|---|
| Formulation example 1. Emulsifiable Concentrate | | | | |
| Compound 1-1 | | | Active Ingredient | 5.0 |
| Toximul H-A | Calcium sulfonate and nonionic surfactant blend | Stepan Co. | Emulsifier | 2.5 |
| Toximul D-A | Calcium sulfonate and nonionic surfactant blend | Stepan Co. | Emulsifier | 7.5 |
| Aromatic 200 | Aromatic hydrocarbon | Exxon Chemical Co. | Solvent | QS to 100% |
| Formulation example 2. Suspension Concentrate | | | | |
| Compound 1-1 | | | Active Ingredient | 10.00 |
| Proylene gylcol | | | Anti-freeze | 5.00 |
| Antifoam 1530 | Silicone defoamer | Dow Corning | Anti-foam | 0.50 |
| Rhodopol 23 | Xanthan gum | Rhone-Poulene | Suspending Aid | 0.25 |
| Morwet D-425 | Napthalene formaldehyde condensate | Witco Corp. | Dispersant | 3.00 |
| Igepal CA-720 | Octylphenol ethoxylate | Rhone-Poulene | Wetting agent | 3.00 |
| Proxel GXL | 1,2 benzisothiazolin-3-one | ICI Americas | Preservative | 0.25 |
| Water | | | Diluent | 68.00 |
| Formulation example 3. Wettable Powder | | | | |
| Compound 1-1 | | | Active Ingredient | 50.00 |
| Geropon T-77 | Sodium-N-methyl-N-oleoyl taurate | Rhone-Poulenc | Wetting agent | 3.00 |
| Lomar PW | Napthalene Sulfonate | Henkel Corp. | Dispersant | 5.00 |
| Kaolin clay | Kaolin clay | J. M. Huber | Filler | 42.00 |
| Formulation example 4. Water Dispersible Granule | | | | |
| Compound 1-1 | | | Active Ingredient | 50.00 |
| Morwet EFW | | Witco Corp. | Wetting agent | 2.00 |
| Morwet D-425 | Napthalene formaldehyde condensate | Witco Corp. | Dispersant | 10.00 |
| ASP 400 | Kaolin Clay | Engelhard Corp. | Filler | 38.00 |

Test Example

A standard greenhouse herbicide activity screening system was used to evaluate the herbicidal efficacy and crop safety of these test compounds. Seven broadleaf weed species including redroot pigweed (*Amaranthus retroflexus*, AMARE), velvetleaf (*Abutilon theophrasti*, ABUTH), sicklepod (*Cassia obtusifolia*, CASOB), ivyleaf morningglory (*Ipomoea hederacea*, IPOHE), lambsquarters (*Chenopodium album*, CHEAL), common ragweed (*Ambrosia artemisiifolia* L., AMBEL), and cocklebur (*Xanthium strumarium*, XANST) were used as test species.

Four grass weed species including green foxtail (*Setaria viridis*, SETVI), barnyardgrass (*Echinochloa crus-galli*, ECHCG), johnsongrass (*Sorghum halepense*, SORHA), and large crabgrass (*Digitaria sanguinalis*, DIGSA) were also used. In addition, three crop species, field corn (*Zea mays* L., var. Dekalb 535, CORN), soybean (*Glycine max* L., var. Pella 86, SOY), and upland rice (Oryza sp., var. Tebonnet, RICE) were included.

Pre-emerge Test

All plants were grown in 10 cm square plastic pots which were filled with a sandy loam soil mix. For pre-emerge tests, seeds were planted one day prior to application of the test compounds. For post-emerge tests, seeds were planted 8–21 days prior to the test to allow emergence and good foliage development prior to application of the test substances. At the time of the post-emerge application, plants of all species were usually at the 2–3 leaf stage of development.

All test compounds were dissolved in acetone and applied to the test units in a volume of 187 l/ha. Test materials were applied at rates ranging from 15 g ai/ha to 1000 g ai/ha using a track sprayer equipped with a TJ8001E even flow flat fan spray nozzle. Plants were arranged on a shelf so that the top of the canopy (post-emerge) or top of the soil surface (pre-emerge) was 40–45 cm below the nozzle. Pressurized air was used to force the test solution through the nozzle as it was mechanically advanced (via electrically driven chain drive) over the top of all test plants/pots. This application simulates a typical commercial field herbicide application.

Post-emerge Test

In the post-emerge test, a commercial non-ionic surfactant was also included (0.25% v/v) to enhance wetting of the leaf surfaces of target plants. Immediately after application, test units of the pre-emerge applications were watered at the soil surface to incorporate the test materials. Subsequently, these test units were bottom-watered. Post-emerge test units were always bottom-watered.

At 14 days after application of the test materials, phytotoxicity ratings were recorded. A rating scale of 0–100 was used as previously described in *Research Methods in Weed Science*, 2nd edition, B. Truelove, Ed., Southern Weed Science Society, Auburn University, Auburn, Ala., 1977. Briefly, "0" corresponds to no damage and "100" corresponds to complete death of all plants in the test unit. This scale was used both to determine efficacy against weed species and damage to crop species. Herbicide activity data for various compounds of this invention, which are shown by compound No. in Tables I–VI, are shown in Tables VIII–IX. The data demonstrate significant differences between compounds for both efficacy against weeds and selectivity for crop species. For selected compounds, excellent activity against a majority of the weed species was observed with minimal damage to at least one of the crop species.

Tables VIII and IX show pre-emerge and post-emerge herbicidal activity data respectively for a few representative examples of the compounds described herein.

TABLE VIII

Pre-emerge Herbicidal Activity

| Cmpd. no. | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| 1-1 | 125 | 100 | 100 | 100 | 100 | 100 | 100 | 100 | 100 | 100 | 100 | 100 | 100 | 100 |
|  | 250 | 100 | 100 | 100 | 100 | 100 | 100 | 100 | 100 | 100 | 100 | 80 | 100 | 100 |
| 1-9 | 125 | 100 | 100 | 70 | 100 | 100 | 99 | 100 | 95 | 95 | 98 | 50 | 8 | 35 |
|  | 250 | 100 | 100 | 99 | 100 | 100 | 100 | 100 | 99 | 99 | 99 | 50 | 8 | 35 |
| 1-15 | 125 | 100 | 100 | 55 | 95 | 100 | 75 | 100 | 50 | 60 | 99 | 0 | 8 | 0 |
|  | 250 | 100 | 100 | 85 | 100 | 100 | 90 | 100 | 65 | 98 | 100 | 35 | 8 | 0 |
| 1-47 | 125 | 100 | 100 | 90 | 95 | 100 | 95 | 100 | 80 | 50 | 95 | 50 | 5 | 15 |
|  | 250 | 100 | 100 | 99 | 98 | 100 | 99 | 100 | 85 | 55 | 100 | 65 | 8 | 25 |
| 1-48 | 125 | 100 | 90 | 0 | 80 | 100 | 70 | 90 | 80 | 55 | 55 | 0 | 0 | 0 |
|  | 250 | 100 | 100 | 0 | 100 | 100 | 70 | 99 | 85 | 85 | 75 | 0 | 5 | 8 |
| 1-49 | 125 | 100 | 95 | 50 | 75 | 100 | 70 | 99 | 45 | 40 | 95 | 0 | 0 | 30 |
|  | 250 | 100 | 100 | 70 | 80 | 100 | 80 | 100 | 98 | 60 | 99 | 0 | 0 | 35 |
| 1-66 | 125 | 100 | 85 | 35 | 90 | 100 | 60 | 99 | 55 | 60 | 90 | 0 | 0 | 40 |
|  | 250 | 100 | 99 | 65 | 100 | 100 | 65 | 100 | 60 | 75 | 99 | 0 | 0 | 45 |
| 1-69 | 125 | 100 | 100 | 100 | 100 | 100 | 100 | 100 | 90 | 95 | 99 | 30 | 5 | 50 |
|  | 250 | 100 | 100 | 99 | 100 | 100 | 100 | 100 | 95 | 95 | 100 | 50 | 10 | 60 |
| 1-70 | 125 | 100 | 100 | 65 | 99 | 100 | 90 | 75 | 85 | 65 | 85 | 30 | 15 | 50 |
|  | 250 | 100 | 100 | 85 | 99 | 100 | 99 | 100 | 95 | 99 | 99 | 80 | 15 | 55 |
| 1-71 | 125 | 100 | 100 | 95 | 100 | 100 | 100 | 100 | 100 | 99 | 100 | 45 | 0 | 50 |
|  | 250 | 100 | 100 | 100 | 100 | 100 | 100 | 100 | 100 | 100 | 100 | 60 | 5 | 65 |
| 1-72 | 125 | 100 | 100 | 65 | 95 | 100 | 95 | 20 | 20 | 60 | 95 | 0 | 5 | 0 |
|  | 250 | 100 | 100 | 100 | 100 | 100 | 95 | 80 | 80 | 60 | 99 | 40 | 8 | 0 |
| 1-73 | 125 | 100 | 100 | 50 | 98 | 100 | 85 | 50 | 0 | 35 | 80 | 0 | 10 | 0 |
|  | 250 | 100 | 100 | 60 | 98 | 100 | 99 | 75 | 0 | 35 | 80 | 15 | 10 | 0 |
| 1-74 | 125 | 100 | 100 | 60 | 100 | 100 | 70 | 90 | 30 | 50 | 99 | 10 | 15 | 50 |
|  | 250 | 100 | 100 | 90 | 100 | 100 | 90 | 100 | 50 | 55 | 100 | 15 | 15 | 60 |
| 2-1 | 125 | 100 | 100 | 100 | 100 | 100 | 100 | 100 | 100 | 100 | 100 | 90 | 50 | 99 |
|  | 250 | 100 | 100 | 100 | 100 | 100 | 100 | 100 | 100 | 100 | 100 | 100 | 65 | 99 |
| 2-16 | 125 | 99 | 55 | 20 | 0 | 100 | 50 | 60 | 35 | 35 | 75 | 0 | 0 | 0 |
|  | 250 | 100 | 60 | 35 | 10 | 100 | 55 | 95 | 60 | 75 | 80 | 0 | 5 | 0 |
| 2-17 | 125 | 99 | 60 | 0 | 30 | 100 | 0 | 85 | 30 | 25 | 60 | 0 | 0 | 0 |
|  | 250 | 100 | 70 | 30 | 50 | 100 | 0 | 98 | 30 | 50 | 80 | 10 | 0 | 0 |
| 2-18 | 125 | 99 | 55 | 20 | 0 | 100 | 50 | 60 | 35 | 35 | 75 | 0 | 0 | 0 |
|  | 250 | 100 | 60 | 35 | 10 | 100 | 55 | 95 | 60 | 75 | 80 | 0 | 5 | 0 |
| 4-1 | 125 | 100 | 65 | 50 | 75 | 100 | 85 | 100 | 90 | 99 | 99 | 0 | 0 | 50 |
|  | 250 | 100 | 95 | 60 | 100 | 100 | 85 | 100 | 99 | 100 | 100 | 0 | 10 | 60 |
| 5-1 | 125 | 100 | 99 | 60 | 99 | 100 | 75 | 100 | 100 | 100 | 100 | 0 | 40 | 55 |
|  | 250 | 100 | 100 | 90 | 100 | 100 | 100 | 100 | 100 | 100 | 100 | 65 | 50 | 80 |

TABLE VIII-continued

Pre-emerge Herbicidal Activity

| Cmpd. no. | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| 6-1 | 125 | 100 | 100 | 100 | 99 | 100 | 100 | 100 | 99 | 100 | 100 | 25 | 40 | 85 |
|  | 250 | 100 | 100 | 100 | 100 | 100 | 100 | 100 | 100 | 100 | 100 | 60 | 50 | 95 |
| 6-2 | 125 | 100 | 100 | 100 | 85 | 100 | 99 | 100 | 99 | 100 | 100 | 25 | 20 | 60 |
|  | 250 | 100 | 100 | 100 | 100 | 100 | 100 | 100 | 100 | 100 | 100 | 40 | 40 | 75 |
| 6-17 | 125 | 100 | 85 | 0 | 0 | 100 | 35 | 100 | 60 | 95 | 99 | 0 | 0 | 25 |
|  | 250 | 100 | 100 | 25 | 0 | 100 | 25 | 100 | 98 | 98 | 100 | 0 | 0 | 35 |
| 6-19 | 250 | 100 | 65 | 75 | 0 | 100 | 50 | 95 | 50 | 65 | 90 | 50 | 0 | 0 |

TABLE IX

Post-emerge Herbicidal Activity

| Cmpd. no | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| 1-1 | 125 | 100 | 100 | 99 | 100 | 100 | 99 | 100 | 100 | 95 | 95 | 100 | 10 | 100 |
|  | 250 | 100 | 100 | 99 | 100 | 100 | 100 | 100 | 100 | 98 | 90 | 100 | 15 | 100 |
| 1-9 | 125 | 100 | 100 | 50 | 100 | 100 | 70 | 60 | 50 | 50 | 50 | 55 | 0 | 0 |
|  | 250 | 100 | 100 | 65 | 100 | 100 | 70 | 70 | 65 | 50 | 60 | 80 | 3 | 0 |
| 1-15 | 125 | 90 | 95 | 60 | 75 | 100 | 55 | 0 | 0 | 0 | 0 | 10 | 5 | 0 |
|  | 250 | 90 | 95 | 65 | 100 | 100 | 55 | 0 | 0 | 0 | 0 | 10 | 5 | 0 |
| 1-47 | 125 | 100 | 100 | 65 | 75 | 99 | 70 | 50 | 60 | 0 | 10 | 15 | 0 | 0 |
|  | 250 | 100 | 100 | 65 | 85 | 100 | 75 | 75 | 65 | 0 | 35 | 40 | 0 | 0 |
| 1-48 | 125 | 100 | 85 | 75 | 80 | 100 | 60 | 50 | 0 | 0 | 25 | 0 | 0 | 0 |
|  | 250 | 100 | 95 | 75 | 75 | 100 | 75 | 60 | 0 | 0 | 50 | 0 | 10 | 35 |
| 1-49 | 125 | 99 | 98 | 75 | 80 | 99 | 70 | 0 | 0 | 0 | 0 | 10 | 0 | 0 |
|  | 250 | 100 | 100 | 75 | 80 | 100 | 70 | 0 | 0 | 0 | 0 | 15 | 0 | 25 |
| 1-66 | 125 | 70 | 90 | 75 | 70 | 98 | 75 | 0 | 0 | 0 | 0 | 10 | 0 | 0 |
|  | 250 | 70 | 90 | 75 | 85 | 100 | 75 | 0 | 0 | 0 | 0 | 10 | 0 | 0 |
| 1-69 | 125 | 99 | 100 | 75 | 100 | 100 | 30 | 0 | 0 | 0 | 0 | 0 | 0 | 0 |
|  | 250 | 100 | 100 | 70 | 100 | 100 | 35 | 30 | 25 | 0 | 30 | 50 | 5 | 0 |
| 1-70 | 125 | 100 | 100 | 65 | 99 | 100 | 60 | 65 | 55 | 0 | 15 | 30 | 0 | 0 |
|  | 250 | 100 | 100 | 65 | 99 | 100 | 65 | 75 | 80 | 25 | 30 | 65 | 0 | 0 |
| 1-71 | 125 | 100 | 100 | 50 | 100 | 100 | 80 | 85 | 35 | 0 | 50 | 50 | 0 | 0 |
|  | 250 | 100 | 100 | 50 | 100 | 100 | 90 | 85 | 65 | 15 | 60 | 75 | 0 | 0 |
| 1-72 | 125 | 80 | 80 | 0 | 60 | 100 | 0 | 0 | 0 | 0 | 0 | 0 | 0 | 0 |
|  | 250 | 90 | 90 | 0 | 60 | 100 | 0 | 0 | 0 | 0 | 0 | 0 | 0 | 0 |
| 1-73 | 125 | 100 | 99 | 55 | 75 | 90 | 70 | 0 | 0 | 0 | 0 | 0 | 0 | 0 |
|  | 250 | 100 | 100 | 60 | 100 | 95 | 75 | 50 | 40 | 0 | 50 | 0 | 0 | 0 |
| 1-74 | 125 | 100 | 100 | 70 | 65 | 80 | 80 | 65 | 60 | 0 | 60 | 50 | 0 | 0 |
|  | 250 | 100 | 100 | 70 | 95 | 80 | 80 | 75 | 65 | 50 | 70 | 70 | 5 | 0 |
| 2-1 | 125 | 100 | 100 | 65 | 80 | 100 | 60 | 70 | 50 | 60 | 55 | 50 | 0 | 15 |
|  | 250 | 100 | 100 | 75 | 99 | 100 | 65 | 80 | 80 | 70 | 55 | 65 | 5 | 40 |
| 2-16 | 125 | 80 | 0 | 0 | 0 | 70 | 0 | 50 | 0 | 0 | 0 | 0 | 0 | 0 |
|  | 250 | 80 | 40 | 0 | 0 | 70 | 0 | 50 | 35 | 0 | 0 | 0 | 0 | 0 |
| 2-17 | 125 | 80 | 95 | 25 | 0 | 95 | 60 | 0 | 0 | 0 | 0 | 0 | 5 | 0 |
|  | 250 | 80 | 98 | 65 | 0 | 95 | 75 | 0 | 25 | 0 | 35 | 25 | 8 | 0 |
| 2-18 | 125 | 80 | 0 | 0 | 0 | 70 | 0 | 50 | 0 | 0 | 0 | 0 | 0 | 0 |
|  | 250 | 80 | 40 | 0 | 0 | 70 | 0 | 50 | 35 | 0 | 0 | 0 | 0 | 0 |
| 4-1 | 125 | 100 | 99 | 55 | 70 | 99 | 30 | 50 | 55 | 50 | 50 | 50 | 5 | 0 |
|  | 250 | 100 | 100 | 55 | 70 | 100 | 60 | 60 | 75 | 75 | 60 | 50 | 15 | 15 |
| 5-1 | 125 | 100 | 100 | 99 | 100 | 100 | 65 | 95 | 75 | 75 | 50 | 65 | 7 | 50 |
|  | 250 | 100 | 100 | 100 | 100 | 100 | 75 | 95 | 65 | 75 | 55 | 55 | 8 | 55 |
| 6-1 | 125 | 100 | 100 | 100 | 100 | 100 | 85 | 100 | 90 | 75 | 90 | 95 | 10 | 90 |
|  | 250 | 100 | 100 | 100 | 100 | 100 | 90 | 100 | 100 | 95 | 98 | 100 | 20 | 95 |
| 6-2 | 125 | 100 | 100 | 100 | 100 | 100 | 85 | 100 | 90 | 80 | 75 | 99 | 15 | 95 |
|  | 250 | 100 | 100 | 100 | 100 | 100 | 90 | 100 | 95 | 95 | 80 | 99 | 15 | 98 |
| 6-17 | 125 | 100 | 100 | 70 | 100 | 100 | 60 | 90 | 60 | 0 | 0 | 70 | 0 | 80 |
|  | 250 | 100 | 100 | 95 | 100 | 100 | 75 | 90 | 65 | 30 | 25 | 70 | 5 | 80 |
| 6-19 | 250 | 100 | 100 | 75 | 100 | 98 | 50 | 65 | 60 | 50 | 50 | 40 | 3 | 35 |

The data in Table X demonstrates improved selectivity for maize for some representative compounds at a rate of 31.3 or 62.5 g a.i./ha.

TABLE X

Post-emerge Herbicidal Activity and Corn Selectivity.

| Cmpd. no. | Rate g ai/ha | AMA-RE | CASOB | CHEAL | AMB-EL | SETVI | CORN |
|---|---|---|---|---|---|---|---|
| 1-1 | 31.3 | 100 | 95 | 100 | 75 | 85 | 8 |
|  | 62.5 | 100 | 99 | 100 | 98 | 99 | 8 |
| 1-48 | 31.3 | 100 | 50 | 80 | 60 | 0 | 0 |
|  | 62.5 | 100 | 75 | 99 | 50 | 30 | 0 |
| 1-49 | 31.3 | 98 | 60 | 98 | 65 | 0 | 0 |
|  | 62.5 | 98 | 70 | 98 | 65 | 0 | 0 |
| 1-69 | 31.3 | 100 | 50 | 80 | 70 | 0 | 0 |
|  | 62.5 | 100 | 65 | 80 | 70 | 50 | 0 |
| 2-1 | 31.3 | 100 | 60 | 100 | 50 | 0 | 0 |
|  | 62.5 | 100 | 60 | 100 | 50 | 60 | 0 |
| 2-17 | 31.3 | 80 | 0 | 90 | 50 | 0 | 0 |
|  | 62.5 | 80 | 0 | 90 | 50 | 0 | 3 |
| 5-1 | 31.3 | 98 | 35 | 100 | 50 | 50 | 0 |
|  | 62.5 | 100 | 85 | 100 | 60 | 60 | 5 |
| 6-2 | 31.3 | 100 | 100 | 100 | 80 | 100 | 3 |
|  | 62.5 | 100 | 100 | 100 | 85 | 100 | 10 |

The data in Table XI and Table XII show the results when compounds 1-1 and 2-1 were tested as mixtures with other herbicides. Observations in Table XI were made 64 days after treatment while those in Table XII were made 56 days after treatment.

TABLE X1

Pre-emerge Herbicidal Activity of Mixtures with Compound 1-1.

| Cmpd. no. | Rate g ai/ha | AMA-RE | ABU-TH | CHEAL | AMB-EL | SET-VI | CORN |
|---|---|---|---|---|---|---|---|
| 1-1. | 50 | 93 | 87 | 95 | 92 | 90 | 0 |
| 1-1. Aceto-chlor | 50 1680 | 95 | 88 | 95 | 93 | 95 | 0 |

TABLE X11

Pre-emerge Herbicidal Activity with of Mixtures with Compound 2-1.

| Cmpd. no. | Rate g ai/ha | AMA-RE | ABU-TH | CHEAL | AMB-EL | SET-VI | CORN |
|---|---|---|---|---|---|---|---|
| 2-1. | 200 | 93 | 95 | 95 | 95 | 90 | 0 |
| 2-1. Aceto-chlor | 200 1680 | 95 | 93 | 95 | 95 | 95 | 0 |

What is claimed is:

1. A compound represented the formula (I) or its salt:

$$I$$

wherein X and Y are independent of each other and represent hydrogen, halogen, cyano, nitro, $(C_{1-4})$alkyl, $(C_{1-4})$haloalkyl, or $(C_{1-4})$haloalkoxy;

Z is oxygen or sulfur;

Q is $$Q1$$

A is oxygen, sulfur, or imino;

$R_1$ is hydrogen, $(C_{1-4})$alkyl, or $(C_{1-4})$haloalkyl;

$R_2$ and $R_3$ are independent of each other and are selected from the group consisting of hydrogen, halogen, cyano, nitro, $(C_{1-4})$alkyl, $(C_{1-4})$haloalkyl, $(C_{2-6})$alkenyl, $(C_{2-6})$haloalkenyl and amino which may be optionally substituted with $(C_{1-4})$alkyl or $(C_{1-4})$haloalkyl;

Ar is a substituted or unsubstituted heterocyclic aromatic ring being at least a five or six membered ring.

2. The compound or its salt according to claim 1 wherein

Ar is a substituted or unsubstituted heterocyclic aromatic ring being at least a five or six membered ring, which can be fused with another substituted or nsubstituted five or six membered carbocyclic or heterocyclic aromatic ring, in which the carbocyclic or heterocyclic aromatic ring may be substituted with up to seven substituents independently selected from the group consisting of halogen, $(C_{1-6})$alkyl, halo$(C_{1-6})$alkyl, $(C_{1-6})$alkoxy, halo$(C_{1-6})$alkoxy, $(C_{1-6})$alkylthio, $(C_{1-6})$alkylsulfonyl, $(C_{1-6})$alkylsulfinyl, $(C_{1-6})$dialkylaminocarbonyl, cyano, nitro, amino, hydroxy, $(C_{1-6})$alkylsulfonylamino, $(C_{1-6})$alkoxycarbonyl$(C_{1-6})$alkoxy, $(C_{1-6})$alkoxycarbonyl-halo$(C_{1-6})$alkyl, $(C_{2-6})$alkenyloxycarbonyl$(C_{1-6})$alkoxy$(C_{1-6})$alkyl, $(C_{1-6})$alkylcarbonylamino, bisbenzoylamino, aminocetyl, aminotrifluroacetyl, and amino$(C_{1-6})$allylsulfonate.

3. The compound or its salt according to claim 1 wherein

X and Y are independently hydrogen or halogen;

Z is oxygen or sulfur;

$R_1$ is $(C_{1-4})$alkyl;

$R_2$ is $(C_{1-4})$haloalkyl;

$R_3$ is hydrogen;

Ar is pyridyl, pyrimidyl, pyridazinyl, triazolyl, thiazolyl isothiazoly, or pyridyl, pyrimidyl, pyridazinyl, triazolyl, thiazolyl or isothiazolyl substituted with up to five substituents independently selected from the group consisting of halogen, $(C_{1-6})$alkyl, $(C_{1-6})$haloalkyl, $(C_{1-6})$alkoxy, $(C_{1-6})$haloalkoxy, $(C_{1-6})$alkylthio, $(C_{1-6})$alkylsulfonyl, $(C_{1-6})$alkylsulfinyl, di$(C_{1-6})$alkylaminocarbonyl, cyano, nitro amino, hydroxy, $(C_{1-6})$alkylsulfonylamino, $(C_{1-6})$alkoxycarbonyl$(C_{1-6})$alkoxy, $(C_{1-6})$alkoxycarbonyl-halo$(C_{1-6})$alkyl, $(C_{2-6})$alkenyloxycarbonyl$(C_{1-6})$alkoxy$(C_{1-6})$alkyl, $(C_{1-6})$alkoxycarbonylamino, bisbenzoylamino, aminoacetyl, aminotrifluoroacetyl, and amino$(C_{1-6})$alkylsulfonate.

4. The compound or its salt according to claim 1 wherein

X is fluorine;

Y is chlorine;

$R_1$ is methyl;

$R_2$ is trifluoromethyl;

Ar is 2-pyridyl, 3-pyridyl, 4-pyridyl, 3-bromo-2-pyridyl, 5-bromo-2-pyridyl, 6-bromo-2-pyridyl, 3-chloro-2-pyridyl, 5-chloro-2-pyridyl, 6-chloro-2-pyridyl, 3-fluoro-2-pyridyl, 5-fluoro-2-pyridyl, 6-fluoro-2-pyridyl, 3-cyano-2-pyridyl, 5-cyano-2-pyridyl, 6-cyano-2-pyridyl, 3-nitro-2-pyridyl, 5-nitro-2-pyridyl, 6-nitro-2-pyridyl, 3-trifluoromethyl-2-pyridyl, 4-trifluoromethyl-2-pyridyl, 5-trifluoromethyl-2-pyridyl, 6-trifluoromethyl-2-pyridyl, 5-amino-2-pyridyl, 3-dimethyl-aminocarbonyl-2-pyridyl,3-methylsulfony-2-pyridyl, 3-isopropylsulfonyl-2-pyridyl, 6-chloro-3-trifluoromethyl-2-pyridyl, 3,5,6-trifluoropyridyl, 2-pyrimidyl, 4-pyrimidyl, 5-bromo-2-pyrimidyl-4-chloro-2-pyrimidyl, 4-trifluoromethyl-2-pyrimidyl, 4,6-dimethoxy-2-pyrimildyl, 2,6,-dimethoxy-4-pyrimidyl, 4,6-dimethoxy-2-trianzinyl, 3-methyl-4-nitro-5-isothiazolyl, or 5-nitro-2-thiazolyl.

5. A process for producing a compound represented by the formula (I) in said claim 1 or its salt, wherein X, Y, Z, and Q are defined therein which comprises reacting a compound represented by formula (II):

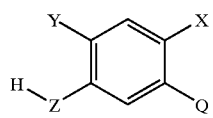

II with a compound of the formula: Ar-Hal wherein Hal is a halogen atom, in the presence of a base.

6. A process for producing a compound or its salt represented by the formula (I) in said claim 1, wherein X, Y, Z, $R_1$, $R_2$, $R_3$, A, and Ar are as defined and Q is Q1 therein which comprises reacting a compound represented by formula (III):

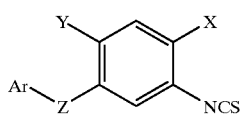

III with a compound of the formula (IV):

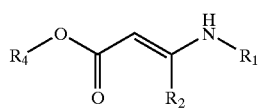

IV wherein $R_1$ and $R_2$ are as defined in claim 1 and $R_4$ represents a $C_{1-4}$alkyl group, in the presence of a base.

7. A process for producing a compound or its salt represented by the formula (I) in said claim 1 wherein X, Y, Z, $R_1$, $R_2$, $R_3$, A, and Ar are as defined therein and Q is $Q_1$ which comprises reacting a compound represented by formula (V):

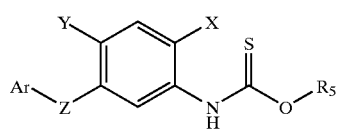

V wherein $R_5$ represents a $C_{1-4}$alkyl or phenyl group;

with a compound of the formula (IV):

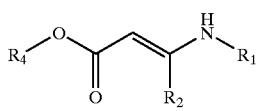

IV wherein $R_1$ and $R_2$ are as defined in claim 1 and $R_4$ represents a $C_{1-4}$ alkyl group, in the presence of a base.

8. A process for producing a compound or its salt represented by the formula (I) in said claim 1 wherein X, Y, Z, $R_1$, $R_2$, $R_3$, A, and Ar are as defined and Q is Q1 therein which comprises reacting a compound represented by formula (VI):

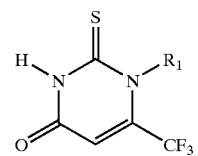

VI with a compound of the formula (VII):

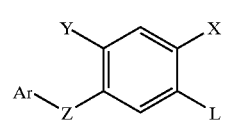

VII wherein $R_1$ is as defined in claim 1;
wherein X, Y, Z, and Ar are as defined in claim 1 and L represents a leaving group, in the presence of a base.

9. A process for producing a compound or its salt represented by the formula (IX) in said claim 1,

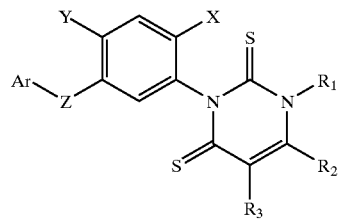

IX which comprises reacting a compound represented by formula (VIII):

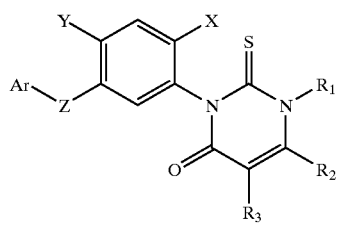

VIII with a thionating agent in the presence of a base, wherein X, Y, Z, $R_1$, $R_2$, $R_3$ and Ar are as defined in claim 1.

10. A process for producing a compound or its salt represented by the formula (I) in said claim 1 wherein X, Y, Z, $R_2$, $R_3$, A, and Ar are as defined, $R_1$ is alkyl, haloalkyl, or amino, and Q is Q1, which comprises reacting a compound represented by formula (VIII) wherein $R_1$ is hydrogen with an alkylating agent or an aminating reagent:

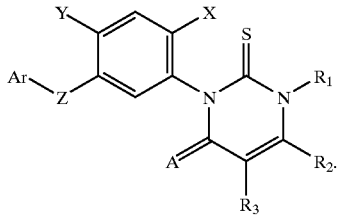

VIII'

11. A process for producing a compound or its salt represented by the formula I wherein X, Y, Z, $R_1$, $R_2$, $R_3$, A, Ar and Q are defined in claim 1, which comprises reacting a haloaryl compound of formula (XII):

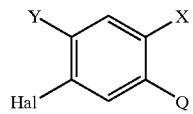

XII wherein hal represents a halogen atom;
with an aryl or heteroaryl hydroxyl compound or thiohydroxy compound, or its salt.

12. A herbicidal compositions, characterized in that it contains at least one compound according to claim 1.

13. A herbicidal composition which comprises an effective amount of a compound of claim 1 and an agricultural adjuvant.

14. A method for controlling weeds, which comprises applying to the locus to be protected a herbicidally effective amount of a compound of claim 1.

15. A method for controlling weeds in a corn field which comprises applying a herbicidally effective amount of a compound of claim 1 to the corn field.

16. A method for controlling weeds in a soybean field which comprises applying a herbicidally effective amount of a compound of claim 1 to the soybean field.

17. A method for controlling weeds, which comprises applying to the locus to be protected a herbicidally effective amount of a compound of claim 1 in combination with another herbicide.

18. A method for controlling weeds of claim 16 wherein the compound of claim 1 is applied to soil as a preemergent herbicide.

19. A method for controlling weeds of claim 14 wherein the compound of claim 1 is applied to plant foliage.

20. A method for controlling weeds of claim 17 wherein the another herbicide is an acetanilide, or sulfonylurea.

21. A method to desiccate a plant which comprises applying to the plant a compound of claim 1.

22. A method to desiccate a plant of claim 21 wherein the plant to which the compound is applied is a potato plant or a cotton plant.

* * * * *